United States Patent
Steele et al.

(10) Patent No.: US 7,273,755 B2
(45) Date of Patent: Sep. 25, 2007

(54) COMPOSITIONS AND METHODS FOR ALTERING BIOSYNTHESIS OF TAXANES AND TAXANE-RELATED COMPOUNDS

(75) Inventors: Christopher L. Steele, Manlius, NY (US); Yijun Chen, Madison, CT (US); Brian A. Dougherty, Killingworth, CT (US); Sandra Hofstead, Berlin, NH (US); Kin S. Lam, San Diego, CA (US); Wenying Li, Middletown, CT (US); Zizhuo Xing, Syracuse, NY (US)

(73) Assignee: Bristol Myers Squibb Co., Princeton, NJ (US)

( * ) Notice: Subject to any disclaimer, the term of this patent is extended or adjusted under 35 U.S.C. 154(b) by 472 days.

(21) Appl. No.: 10/361,290

(22) Filed: Feb. 10, 2003

(65) Prior Publication Data

US 2003/0175913 A1    Sep. 18, 2003

Related U.S. Application Data

(60) Provisional application No. 60/355,144, filed on Feb. 8, 2002.

(51) Int. Cl.
*C12N 5/10* (2006.01)
*C12P 7/52* (2006.01)
*C12N 9/10* (2006.01)
*C12N 9/90* (2006.01)
*C12N 5/04* (2006.01)
*C07H 21/04* (2006.01)

(52) U.S. Cl. .................... 435/375; 435/141; 435/193; 435/233; 435/419; 536/23.2

(58) Field of Classification Search ................ 435/193, 435/375, 410, 419, 132; 536/23.2
See application file for complete search history.

(56) References Cited

U.S. PATENT DOCUMENTS

| | | | |
|---|---|---|---|
| 4,924,011 A | 5/1990 | Denis et al. | |
| 5,015,744 A | 5/1991 | Holton | |
| 5,019,504 A | 5/1991 | Christen et al. | |
| 5,407,816 A | 4/1995 | Bringi et al. | |
| 5,637,484 A | 6/1997 | Yukimune et al. | |
| 5,871,979 A | 2/1999 | Choi et al. | |
| 5,981,777 A | 11/1999 | Durzan et al. | |
| 6,114,160 A | 9/2000 | Croteau et al. | |
| 6,136,989 A | 10/2000 | Foo et al. | |
| 6,248,572 B1 | 6/2001 | Choi et al. | |

FOREIGN PATENT DOCUMENTS

| | | |
|---|---|---|
| EP | 0577274 A | 1/1994 |
| EP | 0 727 492 A2 | 8/1996 |
| GB | 2209526 A | 5/1989 |
| WO | WO93/17121 | 9/1993 |
| WO | WO97/44476 | 11/1997 |

OTHER PUBLICATIONS

Steele et al (2005) Archives of Biochemistry and Biophysics, vol. 438, pp. 1-10.*
Fett-Neto et al. (1994) Biotechnology an Bioengineering, vol. 44, pp. 967-971.*
Yukimune et al. (Nature Biotechnology 1996 14:1129-1132).
Mirjalili and Linden (Biotechnol. Prog. 1996 12:110-118).
Furmanowa et al. (Biotechnology Letters 2000 22:1449-1452).
Fleming et al. J. Am. Chem. Soc. 1994 116: 4137-4138.
Bjorklund and Leete, Phytochemistry 1992 31:3883.
Basic Logic Alignment Search Tool (BLAST; NCBI, Bethesda, MD; Altschul et al. J. Mol. Biol. 215(3)4-3-410 (1990)).
He, X.Z. and Dixon, R.A. The Plant Cell 2000 12(9):1689-1702.
Mahmoud, S.S. and Croteau, R.B. Proc. Natl Acad. Sci. USA 2001 98:8915-8920.
Hewlett-Packard (Palo Alto, CA) sequencing protocols (Miller C. G., Adsorptive Biphasic Column Technology for Protein Sequence Analysis and Protein Chemical Modification. Methods: A Companion to Methods in Enzymology (Academic Press), vol. 6, No. 3, Sep. 1994, pp. 315-333).
Levinsohn et al. (Plant Mol. Bio. Rep. 1994 12(1):20-25 ).
Ausubel et al. (Current protocols of molecular biology. 1987 vol. 1: 1.13.7.
Kevin D. Walker and Heinz G. Floss. J. Am. Chem. Soc., 1998, 120, 5333-5334, "Detection of a Phenylalanine Aminomutase in Cell-Free Extracts of *Taxus brevifolia* and Preliminary Characterization of Its Reaction".
Walker et al., *Taxol Biosynthetic genes*, Phytochemistry, vol. 58, No. 1, Aug. 10, 2001, pp. 1-7.
Hirabayashi Jun et al., *Novel galactose-binding proteins in Annelida: Characterization of 29-kDa tandem repeat-type lectins from the earthworm Lumbricus terrestris*, Journal of Biological Chemistry, vol. 273, No. 23, pp. 14450-14460 (1998).

* cited by examiner

*Primary Examiner*—Elizabeth Slobodyansky
(74) *Attorney, Agent, or Firm*—Sammy G. Duncan, Jr.

(57) ABSTRACT

Isolated nucleic acid and amino acid sequences for phenylalanine aminomutase enzyme and methods for purifying this enzyme are provided. Methods for altering biosynthesis of compounds in plant cell cultures are also provided. In particular, methods for altering production of taxanes and taxane-related compounds are provided.

2 Claims, 9 Drawing Sheets

FIG. 2

```
   1 GCTCTCATAT GGGGTTTGCC GTGGAATCGC GTTCTCACGT AAAGGATATA TTGGGGCTGA
  61 TCAACGCGTT CAACGAGGTG AAGAAAATTA CAGTAGACGG TACGACCCCC ATCACGGTGG
 121 CCCATGTCGC GGCGCTGGCC CGGAGGCATG ACGTGAAGGT TGCGTTGGAG GCGGAGCAAT
 181 GCAGAGCCCG TGTGGAAACC TGCTCTTCGT GGGTGCAGCG CAAGGCGGAA GACGGCGCCG
 241 ACATATACGG CGTCACCACG GGCTTCGGCG CGTGCTCGAG CCGGAGGACC AACCGGCTGA
 301 GCGAGCTGCA GGAGTCGCTC ATACGCTGCC TGCTCGCGGG GGTGTTTACT AAAGGATGCG
 361 CTCCCTCCGT CGACGAGCTC CCCGCGACCG CCACCCGCAG CGCCATGCTG CTCCGCCTTA
 421 ATAGTTTTAC CTATGGATGT TCCGGCATCC GGTGGGAGGT CATGGAAGCG CTGGAAAAGC
 481 TTCTCAACAG CAATGTCTCT CCTAAAGTGC CTCTCCGGGG TTCTGTGAGC GCTTCGGGAG
 541 ACCTCATCCC GCTCGCCTAC ATTGCAGGGC TCCTGATCGG GAAGCCTAGC GTAATCGCTC
 601 GCATAGGCGA CGATGTCGAG GTCCCTGCGC CGAGGCGTT GAGCAGGGTG GGGCTTCGGC
 661 CATTCAAGCT CCAGGCCAAA GAAGGGCTGG CGCTCGTCAA CGGCACCTCC TTCGCCACCG
 721 CGGTCGCCTC CACCGTCATG TACGACGCCA ATGTTCTGTT GCTGCTCGTC GAAACGCTTT
 781 GCGGAATGTT CTGCGAGGTG ATCTTTGGAA GGGAGGAGTT CGCGCATCCG CTGATCCATA
 841 AAGTGAAGCC GCACCCGGGC CAGATCGAAT CGGCGGAGCT GCTCGAGTGG CTGCTGCGGT
 901 CGAGCCCGTT TCAGGAGCTG TCGAGGGAGT ATTACAGTAT TGATAAGCTG AAGAAACCGA
 961 AACAGGATCG CTATGCTCTG AGGTCGAGCC CGCAGTGGTT GGCTCCTCTG GTGCAGACAA
1021 TCAGAGACGC CACCACTACA GTGGAGACGG AGGTCAATTC CGCCAATGAT AACCCCATCA
1081 TTGACCACGC CAATGACAGG GCTCTCCATG GTGCGAATTT CCAGGGCAGC GCCGTCGGTT
1141 TCTACATGGA CTACGTGCGC ATCGCAGTAG CCGGGCTGGG GAAACTCTTG TTCGCTCAGT
1201 TCACGGAGCT GATGATCGAA TATTACAGCA ACGGCCTACC GGGGAACCTC TCCCTGGGGC
1261 CGGACCTGAG CGTGGACTAC GGCCTCAAGG GGCTCGACAT CGCCATGGCC GCCTACAGCT
1321 CCGAGCTTCA GTACCTGGCG AATCCCGTGA CCACACACGT GCACAGCGCG AACAGCACA
1381 ACCAGGACAT CAACTCTCTG GCGCTCATCT CCGCCCGCAA GACGGAGGAG GCGTTGGATA
1441 TCTTAAAGCT CATGATCGCC TCGCATTTAA CAGCAATGTG CCAGGCGGTG GACCTTCGGC
1501 AGCTCGAAGA AGCCCTAGTA AAAGTCGTGG AGAATGTCGT TTCCACCCTT GCAGACGAAT
1561 GCGGCCTCCC TAACGACACA AAGGCGAGGC TTTTATATGT AGCCAAAGCG GTGCCTGTTT
1621 ACACATACCT GGAATCCCCC TGCGACCCCA CGCTTCCCCT CTTGTTAGGC CTGAAACAGT
1681 CCTGTTTCGA TACCATTCTG GCTCTCCACA AAAAAGACGG CATTGAGACG GACACCTTGG
1741 TCGATCGGCT CGCCGAGTTC GAGAAGCGGC TGTCCGACCG CCTGGAAAAC GAGATGACGG
1801 CAGTGAGGGT TTTGTACGAA AAGAAAGGGC ATAAAACGGC AGACAACAAC GACGCCCTCG
1861 TGAGAATCCA GGGTTCCAAA TTCCTTCCTT TTTACAGATT TGTTCGGGAA GAGCTCGACA
1921 CAGGTGTGAT GAGTGCGAGA AGAGAGCAGA CGCCGCAAGA GGACGTGCAG AAAGTGTTCG
1981 ATGCAATTGC CGACGGCAGA ATTACGGTGC CTCTACTGCA CTGCCTGCAA GGGTTTCTCG
2041 GCCAACCAAA TGGGTGCGCC AACGGCGTCT AGTCGTTCCA AAGTGTTTGG AACAAATCTG
2101 CGTGATTTCT GCGTGAATAT TTGAGTAGAA TTTCAGATTG TTCGGTTCGT GTGATGTTTG
2161 CAGTAGAAAT TCCGCAGAAG CGACTGTAGC TTTGCGAGAA TTGTTAGTTT GTGAGTGAAA
2221 TTTATCTGAT TGGCTTCCTA TGTAAACCCT AATTAATTTT TGTTTTAAAA GGATCCC
```

FIG. 3

```
MGFAVESRSH VKDILGLINA FNEVKKITVD GTTPITVAHV AALARRHDVK VALEAEQCRA
RVETCSSWVQ RKAEDGADIY GVTTGFGACS SRRTNRLSEL QESLIRCLLA GVFTKGCAPS
VDELPATATR SAMLLRLNSF TYGCSGIRWE VMEALEKLLN SNVSPKVPLR GSVSASGDLI
PLAYIAGLLI GKPSVIARIG DDVEVPAPEA LSRVGLRPFK LQAKEGLALV NGTSFATAVA
STVMYDANVL LLLVETLCGM FCEVIFGREE FAHPLIHKVK PHPGQIESAE LLEWLLRSSP
FQELSREYYS IDKLKKPKQD RYALRSSPQW LAPLVQTIRD ATTTVETEVN SANDNPIIDH
ANDRALHGAN FQGSAVGFYM DYVRIAVAGL GKLLFAQFTE LMIEYYSNGL PGNLSLGPDL
SVDYGLKGLD IAMAAYSSEL QYLANPVTTH VHSAEQHNQD INSLALISAR KTEEALDILK
LMIASHLTAM CQAVDLRQLE EALVKVVENV VSTLADECGL PNDTKARLLY VAKAVPVYTY
LESPCDPTLP LLLGLKQSCF DTILALHKKD GIETDTLVDR LAEFEKRLSD RLENEMTAVR
VLYEKKGHKT ADNNDALVRI QGSKFLPFYR FVREELDTGV MSARREQTPQ EDVQKVFDAI
ADGRITVPLL HCLQGFLGQP NGCANGV
```

FIG. 4

```
   1  TTCAGTTTTA TCTCGCTCAA GTTTCAATCT TTTAATTTTA AAGTTATTTT CCTTGCTCTG
  61  CGATGGGGTT TGCCGTGGAA TCGCGTTCTC ACGTAAAGGA TATATTGGGG CTGATCAACG
 121  CGTTCAACGA GGTGAAGAAA ATTACAGTAG ACGGTACGAC CCCCATCACG GTGGCCCATG
 181  TCGCGGCGCT GGCCCGGAGG CATGACGTGA AGGTTGCGTT GGAGGCGGAG CAATGCAGAG
 241  CCCGTGTGGA AACCTGCTCT TCGTGGGTGC AGCGCAAGGC GGAAGACGGC GCCGACATAT
 301  ACGGCGTCAC CACGGGCTTC GGCGCGTGCT CGAGCCGGAG GACCAACCAG CTGAGCGAGC
 361  TGCAGGAGTC GCTCATACGC TGCCTGCTCG CGGGGGTGTT TACTAAAGGA TGCGCTTCCT
 421  CCGTCGACGA GCTCCCCGCG ACCGCCACCC GCAGCGCCAT GCTGCTCCGC CTTAATAGTT
 481  TTACCTATGG ATGTTCCGGC ATCCGGTGGG AGGTCATGGA AGCGCTGGAA AAGCTTCTCA
 541  ACAGCAATGT CTCTCCTAAA GTGCCTCTCC GGGGTTCTGT GAGCGCTTCG GGAGACCTCA
 601  TCCCGCTCGC CTACATTGCA GGGCTCCTGA TCGGGAAGCC TAGCGTAATC GCTCGCATAG
 661  GCGACGATGT CGAGGTCCCT GCGCCCGAGG CGTTGAGCAG GGTGGGGCTT CGGCCATTCA
 721  AGCTCCAGGC CAAAGAAGGG CTGGCGCTCG TCAACGGCAC CTCCTTCGCC ACCGCGGTCG
 781  CCTCCACCGT CATGTACGAC GCCAATGTTC TGTTGCTGCT CGTCGAAACG CTTTGCGGAA
 841  TGTTCTGCGA GGTGATCTTT GGAAGGGAGG AGTTCGCGCA TCCGCTGATC CATAAAGTGA
 901  AGCCGCACCC GGGCCAGATC GAATCGGCGG AGCTGCTCGA GTGGCTGCTG CGGTCGAGCC
 961  CGTTTCAGGA GCTGTCGAGG GAGTATTACA GTATTGATAA GCTGAAGAAA CCGAAACAGG
1021  ATCGCTATGC TCTGAGGTCG AGCCCGCAGT GGTTGGCTCC TCTGGTGCAG ACAATCAGAG
1081  ACGCCACCAC TACAGTGGAG ACGGAGGTCA ATTCCGCCAA TGATAACCCC ATCATTGACC
1141  ACGCCAATGA CAGGTAATGT ATATCATTCG TCGTTAAGCA ATCTGCCGAC TTCATAGAGA
1201  TTCCAAAACT TCTGACGAAA AAGTGGATAA GACGGGGCTC CTAGAAAGTT TTCCTTTTAA
1261  AGATGAACTA TATTTTTTTA TTACGGACTA GATTTCGACG GTTTTGTCCG ATCCATTGGC
1321  AGGGCTCTCC ATGGTGCGAA TTTCCAGGGC AGCGCCGTCG GTTTCTACAT GGACTACGTG
1381  CGCATCGCAG TCGCCGGGCT GGGGAAACTC TTGTTCGCTC AGTTCACGGA GCTGATGATC
1441  GAATATTACA GCAACGGCCT ACCGGGGAAC CTCTCCCTGG GGCCGGACCT GAGCGTGGAC
1501  TACGGCCTCA AGGGGCTCGA CATCGCCATG GCCGCCTACA GCTCCGAGCT TCAGTACCTG
1561  GCGAATCCCG TGACCACACA CGTGCACAGC GCGGAACAGC ACAACCAGGA CATCAACTCT
1621  CTGGCGCTCA TCTCCGCCCG CAAGACGGAG GAGGCGTTGG ATATCTTAAA GCTCATGATC
1681  GCCTCGCATT TAACAGCAAT GTGCCAGGCG GTGGACCTTC GGCAGCTCGA AGAAGCCCTA
1741  GTAAAAGTCG TGGAGAATGT CGTTTCCACC CTTGCAGACG AATGCGGCCT CCCTAACGAC
1801  ACAAAGGCGA GGCTTTTATA TGTAGCCAAA GCGGTGCCTG TTTACACATA CCTGGAATCC
1861  CCCTGCGACC CCACGCTTCC CCTCTTGTTA GGCCTGAAAC AGTCCTGTTT CGATACCATT
1921  CTGGCTCTCC ACAAAAAAGA CGGCATTGAG ACGGACACCT TGGTCGATCG GCTCGCCGAG
1981  TTCGAGAAGC GGCTGTCCGA CCGCCTGGAA AACGAGATGA CGGCAGTGAG GGTTTTGTAC
2041  GAAAAGAAAG GGCATAAAAC GGCAGACAAC AACGACGCCC TCGTAAGAAT CCAGGGTTCC
2101  AAATTCCTTC CTTTTTACAG ATTTGTTCGG GAAGAGCTCG ACACAGGTGT GATGAGTGCG
2161  AGAAGAGAGC AGACGCCGCA AGAGGACGTG CAGAAAGTGT TCGATGCAAT TGCCGACGGC
2221  AGAATTACGG TGCCTCTGCT GCACTGCCTG CAAGGGTTTC TCGGCCAACC AAATGGGTGC
2281  GCCAACGGCG TCTAGTCGTT CCAAAGTGTT TGGAACAAAT CTGCGTGATT CTGCGTGAAA
2341  TATTTCAGTA GAATTTCAGA TTGTTCGGTT CGTGTGATGT TTGCAGTAGA AATTCCGCAG
2401  AAGCGACTGT A
```

FIG. 5

```
   1  ATGGGGTTTG CCGTGGAATC GCGTTCTCAC GTAAAGGATA TATTGGGGCT GATCAACACG
  61  TTCAACGAGG TGAAGAAAAT TACAGTAGAC GGTACGACCC CCATCACGGT GGCCCATGTC
 121  GCGGCGCTGG CCCGGAGGCA TGACGTGAAG GTTGCGTTGG AGGCGGAGCA ATGCAGAGCC
 181  CGTGTGGAAA CCTGCTCTTC GTGGGTGCAA CGCAAGGCGG AAGACGGCGC CGACATATAC
 241  GGCGTCACCA CGGGCTTCGG CGCGTGCTCG AGCCGGAGGA CCAACCAGCT GAGCGAGCTG
 301  CAGGAGTCGC TCATACGCTG CCTGCTCGCG GGGGTGTTTA CTAAAGGATG CGCTTCCTCC
 361  GTCGACGAGC TCCCCGCGAC CGTCACCCGC AGCGCCATGC TGCTCCGCCT TAATAGTTTT
 421  ACCTATGGAT GTTCCGGCAT CCGGTGGGAG GTCATGGAAG CGCTGGAAAA GCTTCTCAAC
 481  AGCAATGTCT CTCCTAAAGT GCCTCTCCGA GGATCTGTGA GCGCTTCGGG AGACCTCATC
 541  CCGCTCGCCT ACATTGCAGG GCTCCTGATC GGGAAACCTA GCGTAATCGC TCGCATAGGC
 601  GACGATGTCG AGGTCCCTGC GCCCGAGGCG TTGAGCAGGG TGGGGCTGCG GCCATTCAAG
 661  CTCCAGGCCA AGAAGGGCT GGCGCTCGTC AACGGCACCT CCTTCGCCAC CGCGCTCGCC
 721  TCCACCGTCA TGTACGACGC CAATGTTCTG TTGCTGCTCG TCGAAACGCT TTGCGGAATG
 781  TTCTGCGAGG TGATCTTTGG AAGGGAGGAG TTCGCGCATC CGCTGATCCA TAAAGTGAAG
 841  CCGCACCCGG GCCAGATCGA ATCGGCGGAG CTGCTCGAGT GGCTGCTGCG GTCGAGCCCG
 901  TTTCAGGAGC TGTCGAGGGA GTATTACAGT ATTGATAAGC TGAAGAAACC GAAACAGGAT
 961  CGCTATGCTC TGAGGTCGAG CCCGCAGTGG TTGGCTCCTC TGGTGCAGAC AATCAGAGAC
1021  GCCACCACTA CAGTGGAGAC GGAGGTCAAT TCCGCCAATG ATAACCCCAT CATTGACCAC
1081  GCCAATGACA GGTAATGTAC ATCATTCGTC GTTAAGCAAT CTGCCGACTT CATAGAGATT
1141  CCAAAACTTC TGACAAAAAA GTGGATAAGA TGGGGCTCCT AGAAAGTTTT CCTTTTAAAG
1201  ATGAACTATA TTTTTTTATA ACTGACTAGA TTTCGCTGGT TTTGTCCGAT CCATTGGCAG
1261  GGCTCTCCAT GGTGCGAATT CCAGGGCAG CGCCGTCGGC TTCTACATGG ACTACGTGCG
1321  CATCGCAGTC GCCGGGCTGG GGAAACTCTT GTTCGCTCAG TTCACGGAGC TGATGATCGA
1381  ATATTACAGC AACGGCCTAC CGGGGAACCT CTCCCTGGGG CCGGACCTGA GCGTGGACTA
1441  CGGCCTCAAG GGGCTCGACA TCGCCATGGC CGCCTACAGC TCCGAGCTTC AGTACCTGGC
1501  GAATCCCGTG ACCACACACG TGCACAGCGC GGAACAGCAC AACCAGGACA TCAACTCTCT
1561  GGCGCTCATC TCCGCCCGCA AGACGGATGA GGCGTTGGAT ATCTTAAAGC TCATGATCGC
1621  CTCGCATTTA ACAGCAATGT GCCAGGCGGT GGACCTTCGG CAGCTCGAAG AAGCCCTAGT
1681  AAAAGTCGTG GAGAATGTCG TTTCCACCCT TGCAGACGAA TGCGGCCTCC CTAACGACAC
1741  AAAGGCGAGG CTTTTATATG TAGCCAAAGC GGTGCCTGTT TACACATACC TGGAATCCCC
1801  CAGCGACCCC ACGCTTCCCC TCTTGTTAGG CCTGAAACAA TCCTGTTTCG ATTCCATTCT
1861  GGCTCTCCAC AAAAAAGACG GAATTGAGAC GGACACCTTG GTCGATCGGC TCGCCGAGTT
1921  CGAGAAGCGG CTGTCCGACC GCCTGGAAAA CGAGATGACG GCAGTGAGGG TTTTGTACGA
1981  AAAGAAAGGG CATAAAACGG CAGACAACAA CGACGCCCTC GTGAGAATCC AGGGTTCCAA
2041  ATTCCTTCCT TTTTACAGAT TTGTTCGGGA CGAGCTCGAC ACAGGTGTGA TGAGTGCGAG
2101  AAGAGAGCAG ACGCCGCAAG AGGACGTGCA GAAAGTGTTC GATGCAATTG CCGACGGCAG
2161  AATTACGGTG CCTCTGCTGC ACTGCCTGCA AGGGTTTCTC GGCCAACCAA ATGGGTGCGC
2221  CAACGGCGTC TAG
```

FIG. 6

```
   1  ATGGGGTTTG  CCGTGGAATC  GCGTTCTCAC  GTAAAGGATA  TATTGGGGCT  GATCAACACG
  61  TTCAACGAGG  TGAAGAAAAT  TACAGTAGAC  GGTACGACCC  CCATCACGGT  GGCCCATGTC
 121  GCGGCGCTGG  CCCGGAGGCA  TGACGTGAAG  GTTGCGTTGG  AGGCGGAGCA  ATGCAGAGCC
 181  CGTGTGGAAA  CCTGCTCTTC  GTGGGTGCAG  CGCAAGGCGG  AAGACGGCGC  CGACATATAC
 241  GGCGTCACCA  CGGGCTTTGG  CGCGTGCTCG  AGCCGGAGGA  CCAACCAGCT  GAGCGAGCTG
 301  CAGGAGTCGC  TTATACGCTG  CCTGCTCGCG  GGGGTGTTTA  CTAAAGGATG  CGCTTCCTCC
 361  GTCGACGAGC  TCCCTGCGAC  CGTCACCCGC  AGCGCCATGC  TGCTCCGCCT  TAATAGTTTT
 421  ACCTATGGAT  GTTCCGGCAT  CCGGTGGAG   GTCATGGAAG  CGCTGGAAAA  GCTTCTCAAC
 481  AGCAATGTCT  CTCCTAAAGT  GCCTCTCCGA  GGATCTGTGA  GCGCTTCGGG  AGACCTCATC
 541  CCGCTCGCCT  ACATTGCAGG  GCTCCTGATT  GGGAAGCCTA  GCGTAATCGC  TCGCATAGGC
 601  GACGATGTCG  AGGTCCCTGC  GCCCGAGGCG  TTGAGCAGGG  TGGGGCTGCG  GCCATTCAAG
 661  CTCCAGGCCA  AGAAGGGCT   GGCGCTCGTC  AACGGCACCT  CCTTCGCCAC  CGCGCTCGCC
 721  TCCACCGTCA  TGTACGACGC  CAATGTTCTG  TTGCTGCTAG  TCGAAACGCT  TTGCGGAATG
 781  TTCTGCGACG  TGATCTTTGG  AAGGGAGGAG  TTCGCGCATC  CGCTGATCCA  TAAAGTGAAG
 841  CCGCACCCAG  GCCAGATCGA  ATCGGCGGAG  CTGCTCGAGT  GGCTGCTGCG  GTCGAGCCCG
 901  TTTCAGGACC  TGTCGAGGGA  GTATTACAGT  ATTGATAAGC  TGAAGAAACC  GAAACAGGAT
 961  CGCTATGCTC  TGAGGTCGAG  CCCGCAGTGG  TTGGCTCCTC  TGGTGCAGAC  AATCAGAGAC
1021  GCCACCACTA  CAGTGGAGAC  GGAGGTCAAT  TCCGCCAATG  ATAACCCCAT  CATTGACCAC
1081  GCCAATGACA  GGTAATGCAT  ATCATTCGTC  GTTAAGCAAT  CTGCCGACTT  CATAGAGATT
1141  CCAAAACTTC  TGACAAAAAA  GTGGATAAGA  TGGGGCTCCT  AGAAAGTTTT  CCTTTTAAAG
1201  ATGAACTATA  TTTTTTATA   ACTGACTAGA  TTTCGCTGGT  TTTGTCCGAT  CCATTGGCAG
1261  GGCTCTCCAT  GGTGCGAATT  CCAGGGCAG   CGCCGTCGGC  TTCTACATGG  ACTACGTGCG
1321  CATCGCAGTC  GCCGGGCTGG  GGAAACTCTT  GTTCGCTCAG  TTCACGGAGC  TGATGATCGA
1381  ATATTACAGC  AACGGCCTAC  CGGGGAACCT  CTCCCTGGGG  CCGGACCTGA  GCGTGGACTA
1441  CGGCCTCAAG  GGGCTCGACA  TCGCCATGGC  CGCCTACAGC  TCCGAGCTTC  AGTACCTGGC
1501  GAATCCCGTG  ACCACACACG  TGCACGCGC   GGAACAGCAC  AACCAGGACA  TCAACTCTCT
1561  GGCGCTCATC  TCCGCCCGCA  AGACGGATGA  GGCGTTGGAT  ATCTTAAAGC  TCATGATCGC
1621  CTCGCATTTA  ACAGCAATGT  GCCAGCGGT   GGACCTTCGG  CAGCTCGAAG  AAGCCCTAGT
1681  AAAAGTCGTG  GAGAATGTCG  TTTCCACCCT  TGCAGACGAA  TGCGGCCTCC  CTAACGACAC
1741  AAAGGCGAGG  CTTTTATATG  TAGCCAAAGC  GGTGCCTGTT  TACACATACC  TGGAATCCCC
1801  CTGCGACCCT  ACGCTTCCCC  TCTTGTTAGG  CCTGAAACAG  TCCTGTTTCG  ATTCCATTCT
1861  GGCTCTCCAC  AAAAAAGACG  GCATTGAGAC  GGACACCTTG  GTGGATCGGC  TCGCCGAGTT
1921  CGAGAAGCGG  CTGTCCGACC  GCCTGGAAAA  CGAGATGACG  GCAGTGAGGG  TTTTGTACGA
1981  AAAGAAAGGG  CATAAAACTG  CAGACAACAA  CGACGCCCTC  GTGAGAATCC  AGGGTTCCAA
2041  ATTCCTTCCT  TTTTACAGAT  TTGTTCGGGA  CGAGCTCGAC  ACAGGTGTGA  TGAGTGCGAG
2101  AAGAGAGCAG  ACGCCGCAAG  AGGACGTGCA  GAAAGTGTTC  GATGCAATTG  CCGACGGCAG
2161  AATTACGGTG  CCTCTGCTGC  ACTGCCTGCA  AGGGTTTCTC  GGCCAACCAA  ATGGGTGCGC
2221  CAACGGCGTC  TAGAC
```

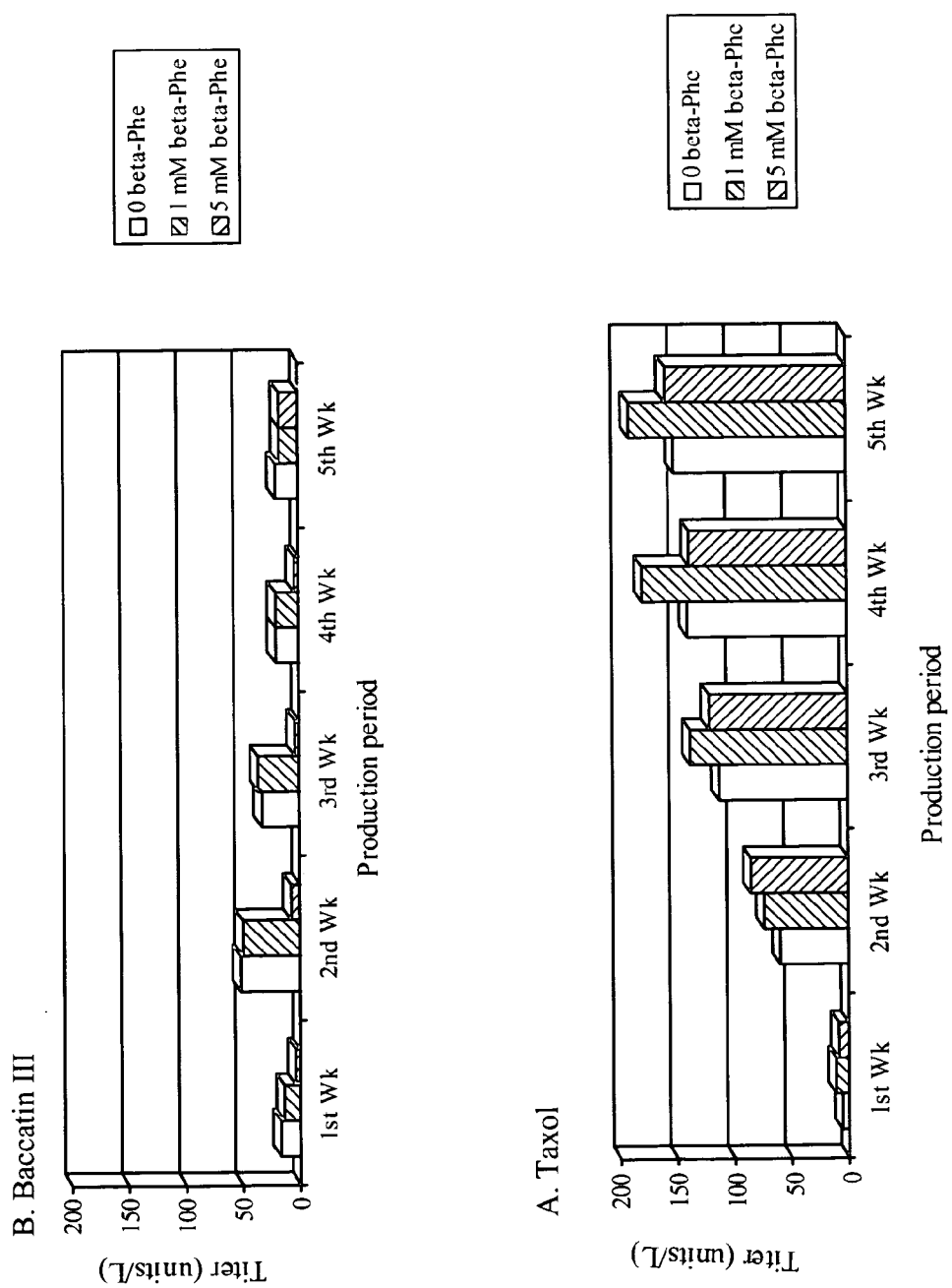

FIG. 9 pam 1 MGFAVE--------------------------------SRSHVKDILGLINAFNEVKKITVDGTTPITVAHVAALAR
pal 1 MVAAAEITQANEVQVKSTGLCTDFGSSGSDPLNWVRAAKAMEGSHFEEVKAMVDSYFGAKEISIEGKS-
LTISDVAAVAR pam 46
RHDVKVALEAEQCRARVETCSSWVQRKAEDGADIYGVTTGFGACSSRRTNRLSELQESLIRCLLAGVFTKGCAPSVDELP
pal 80 RSQVKVKLDAAAAKSRVEESSNWVLTQMTKGTDTYGVTTGFGATSHRRTNQGAELQKELIRFLNAGVLGK-CPENV-
-LS pam 126
ATATRSAMLLRLNSFTYGCSGIRWEVMEALEKLLNSNVSPKVPLRGSVSASGDLIPLAYIAGLLIGKPSVIARIGDDVEV
pal 157
EDTTRAAMLVRTNTLLQGYSGVRWDILETVEKLLNAWLTPKLPLRGTITASGDLVPLSYIAGLLTGRPNSRVRSRDGIEM pam 206 PAPEALSRVGL-
RPFKLQAKEGLALVNGTSFATAVASTVMYDANVLLLLVETLCGMFCEVIFGREEFAHPLIHKVKPHPG
pal 237
SGAEALKKVGLEKPFELQPKEGLAIVNGTSVGAALASIVCFDANVLALLSEVISAMFCEVMNGKPEFTDPLTHKLKHHPG pam 285
QIESAELLEWLLRSSPFQELSREYYSIDKLKKPKQDRYALRSSPQWLAPLVQTIRDATTTVETEVNSANDNPIIDHANDR
pal 317
QMEAAAIMEYVLDGSSYMKHAAKLHEMNPLQKPKQDRYGLRTSPQWLGPQVEIIRSATHMIEREINSVNDNPVIDVARDK pam 365
ALHGANFQGSAVGFYMDYVRIAVAGLGKLLFAQFTELMIEYYSNGLPGNLSLGPDLSVDYGLKGLDIAMAAYSSELQYLA
pal 397
ALHGGNFQGTPIGVSMDNLRLSISAIGKLMFAQFSELVNDYYNGGLPSNLSGGPNPSLDYGLKGAEIAMASYTSELLYLA pam 445 NPVTTHVHSAEQHNQDINSLALISARKTEEALDILKLMIASHLTAMCQAVDLRQLEEALVKVVENVVSTLADEC---
GLP
pal 477
NPVTSHVQSAEQHNQDVNSLGLVSARKSAEAIDILKLMLSTYLTALCQAVDLRHLEENMLATVKQIVSQVAKKTLSTGLN pam 522 NDT------KARLLYVAKAVPVYTYLESPCDPTLPLLLGLKQSCFDTILALHKKDGIETDTLVDRLAEFEKRLSDRLENE
pal 557
GELLPGRFCEKDLLQVVDNEHVFSYIDDPCNASYPLTQKLRNILVEHAFKNAEGEKDPNTSIFNKIPVFEAELKAQLEPQ pam 596
MTAVRVLYEKKGHKTADNNDALVRIQGSKFLPFYRFVREELDTGVMSARREQTPQEDVQKVFDAIADGRITVPLLHCLQG
pal 637 VSLARESYDKGTSPLPD------RIQECRSYPLYEFVRNQLGTKLLSGTRTISPGEVIEVVYDAISEDKVIVPLFKCLDG pam 676 FLG-----------QP--NGCANGV-----------------
pal 711 WKGTLAHSEINNLPRSPLYNDCYDLSPRMLLLMLLFSDPEFDWS

COMPOSITIONS AND METHODS FOR ALTERING BIOSYNTHESIS OF TAXANES AND TAXANE-RELATED COMPOUNDS This application claims a benefit of priority from U.S. application Serial No. 60/355,144 filed Feb. 8, 2002, the entire disclosure of which is herein incorporated by reference.

FIELD OF THE INVENTION

The present invention provides isolated nucleic acid and deduced amino acid sequences for phenylalanine aminomutase enzyme as well as methods for purification of this enzyme. Also provided are methods of using the phenylalanine aminomutase gene of this enzyme to alter biosynthesis of compounds in plant cell cultures. For example, transferring the phenylalanine aminomutase gene to Taxus plant cells alters biosynthesis of taxanes and taxane-related compounds by these cells. The invention also relates to methods for altering the production of taxanes and taxane-related compounds in vivo by supplying to the cell β-phenylalanine alone or in combination with benzoic acid or a salt thereof in the production medium.

BACKGROUND OF THE INVENTION

Paclitaxel is a useful therapeutic agent for various cancers including, but not limited to, ovarian cancer, breast cancer, and lung cancer. This taxane-type diterpene was first identified after isolation from *Taxus brevifolia* NUTT, a plant belonging to the genus *Taxus*, family Taxaceae. While paclitaxel can be found in all parts of the plant body, the bark has been found to have the highest concentration. At present, paclitaxel is collected from a natural or cultivated plant body. However, plants belonging to the genus *Taxus* grow very slowly, taking more than 10 years to grow to a height of 20 cm above the ground. Further, stripping of the bark generally results in tree death. Thus, isolating from natural sources the large amounts of paclitaxel needed for therapeutic uses is extremely difficult, if not impossible.

Attempts have been made to chemically synthesize paclitaxel. However, paclitaxel is a large, structurally complex molecule and large scale synthesis from simple, available chemicals is currently not a viable commercial alternative.

Semi-synthetic production via chemical attachment of a side chain to the agriculturally produced paclitaxel precursor, 10-deacetyl baccatin, has also been proposed (U.S. Pat. No. 4,924,011; U.S. Pat. No. 5,015,744). 10-Deacetyl baccatin is obtained from the needles of trees of the *Taxus* species. However, obtaining this precursor is by no means trivial and 10-deacetyl baccatin content of the needles may not be as high as initially reported. Thus, semi-synthetic production is expensive and also unlikely to be able to supply the necessary amount of paclitaxel required for its chemotherapeutic applications.

The most promising means for producing sufficient amounts of paclitaxel necessary for therapeutic applications is through plant cell cultures.

A variety of methods for producing paclitaxel and other taxanes or taxane-related compounds via cultured plant cells have been described.

U.S. Pat. No. 5,019,504 describes a method for producing paclitaxel and derivatives thereof via cultured cells of *Taxus brevifolia*. However, the yield from this method ranges between 1 to 3 mg/L and is insufficient for industrial applications.

U.S. Pat. No. 5,015,744 describes a method for production of baccatin III via plant cell culture, which can then be used in semi-synthetic production of paclitaxel.

U.S. Pat. No. 5,407,816 and WO 93/17121 describe a method for producing paclitaxel and paclitaxel-like compounds from *Taxus* cells inoculated on a nutrient medium. In this method, paclitaxel is produced in an amount of at least 10-fold greater than that produced by native *Taxus* cells. Using this method, *Taxus chinensis* cells produced a yield of 153 mg/L of paclitaxel and taxanes. However, the requirements of the nutrient media are quite complicated and growth conditions are quite limited, thus rendering industrial applicability of this method also questionable.

Methods for increasing paclitaxel production via addition of stimulators to plant cell culture medium have also been proposed. For example, U.S. Pat. No. 5,637,484 describes a method for increasing paclitaxel production by addition of jasmonate and Ag-containing compounds to the culture medium. Addition of methyl jasmonate to increase production of paclitaxel in *Taxus* cell cultures was also disclosed by Yukimune et al. (Nature Biotechnology 1996 14:1129-1132) and Mirjalili and Linden (Biotechnol. Prog. 1996 12:110-118). WO 97/44476 describes methods for producing paclitaxel, baccatin III and other paclitaxel-like compounds in high yield from *Taxus* cells cultured with enhancement agents such as silver ion or complex, jasmonic acid, auxin-related growth regulators, and inhibitors of the phenylpropanoid pathway such as 3,4-methylenedioxy-6-nitrocinnamin acid. U.S. Pat. No. 5,871,979 describes a method for producing paclitaxel in high yields from semi-continuous cultures of *Taxus* genus plant wherein the plant cells are inoculated on a medium containing sugar. U.S. Pat. No. 6,248,572 also describes methods for producing paclitaxel in large amounts by culturing *Taxus* genus plant cells in a culture medium containing sugar alone or sugar in combination with $AgNO_3$. EP 0 727 492 A2 describes a method for producing taxane-type diterpenes in a plant cell or tissue by culturing the cell or tissue in the presence of a coronatine, a bacterium which produces a coronatine, a culture solution or a culture extract of such bacterium, cyclic polysaccharides, fatty acids or an imino or amino derivative of jasmonic acid. Furmanowa et al. (Biotechnology Letters 2000 22:1449-1452) describe methods for increasing paclitaxel production in *Taxus cuspidate* cell culture via addition of vanadyl sulfate, phenylalanine, or chitosan and methods for increasing baccatin III production in *Taxus media* cell culture via addition of aminobenzoic acid. Additionally, studies performed to reveal compounds that may enhance paclitaxel production in vivo suggest that β-phenylalanine may increase paclitaxel production; however, in the production study only a mixture of α and β-phenylalanine is fed. β-phenylalanine alone was not used (WO 97/44476).

SUMMARY OF THE INVENTION

An object of the present invention is to provide methods for purifying phenylalanine aminomutase from plant cells. In a preferred embodiment, the phenylalanine aminomutase is purified from plant cells of a *Taxus* sp.

Another object of the present invention is to provide purified phenylalanine aminomutase.

Another object of the present invention is to provide isolated nucleic acid sequences encoding phenylalanine aminomutase enzyme.

Another object of the present invention is to provide vectors comprising a nucleic acid encoding a phenylalanine aminomutase enzyme and host cells comprising these vectors which express a phenylalanine aminomutase enzyme.

Another object of the present invention is to provide methods for altering biosynthesis of compounds by plant cell cultures via genetic transformation of phenylalanine aminomutase genes. In one embodiment of the present invention, phenylalanine aminomutase gene is genetically transformed into plant cells, preferably *Taxus* plant cells, to alter biosynthesis of taxanes and taxane-related compounds. In this embodiment, a vector comprising a nucleic acid sequence encoding phenylalanine aminomutase may be transformed into the cells so that expression of phenylalanine aminomutase is increased.

Another object of the present invention is to provide methods for altering levels of taxanes and taxane-related compounds in plant cell cultures which comprise culturing the plant cells with β-phenylalanine (3-amino-3-phenylpropionic acid). In a preferred embodiment, this method further comprises adding benzoic acid or a salt thereof to the plant cell cultures.

Another object of the present invention is to provide methods for altering the ratio of paclitaxel to baccatin III in plant cell cultures, which comprises culturing the plant cells with β-phenylalanine and/or benzoic acid or a salt thereof.

Yet another object of the present invention is to provide methods of using the purified phenylalanine aminomutase and/or isolated nucleic acid sequences encoding phenylalanine aminomutase enzyme to identify phenylalanine aminomutase genes in other species, to identify mutations in phenylalanine genes which alter the biocatalytic properties of the protein encoded by these genes, and to isolate genomic sequences adjacent to the phenylalanine aminomutase gene in a plant cell.

BRIEF DESCRIPTION OF THE FIGURES

FIG. 2 provides a nucleic acid sequence (SEQ ID NO: 1) encoding phenylalanine aminomutase which begins at nucleotide 9 and ends at nucleotide 2069.

FIG. 3 provides the deduced amino acid sequence (SEQ ID NO: 2) of phenylalanine aminomutase.

FIG. 4 provides a nucleic acid sequence of a phenylalanine aminomutase (PAM) genomic polymerase chain reaction (PCR) product (SEQ ID NO: 3) from *T. chinensis*. The starting methionine codon (ATG) begins at nucleotide 63, the stop codon (TAG) begins at nucleotide 2293 and the entire fragment is 2411 nucleotides in length. The genomic fragment contains an intron that begins at nucleotide 1154 and ends at nucleotide 1322.

FIG. 5 provide a nucleic acid sequence of a phenylalanine aminomutase genomic PCR product (SEQ ID NO: 4) from *T. media*. The starting methionine codon (ATG) begins at nucleotide 1, the stop codon (TAG) begins at nucleotide 2231 and the entire fragment is 2233 nucleotides in length. The genomic fragment contains an intron that begins at nucleotide 1091 and ends at nucleotide 1260.

FIG. 6 provide a nucleic acid sequence of a phenylalanine aminomutase genomic PCR product (SEQ ID NO: 5) from *T. canadensis*. The starting methionine codon (ATG) begins at nucleotide 1, the stop codon (TAG) begins at nucleotide 2231 and the entire fragment is 2235 nucleotides in length. The genomic fragment contains an intron that begins at nucleotide 1091 and ends at nucleotide 1260.

FIG. 7 is a bargraph showing the effects of DL-β-phenylalanine (DL-3-amino-3-phenylpropionic acid) on paclitaxel and baccatin III production in batch cultivation of *T. chinensis* cells. Each value represents the average of four samples. FIG. 7A shows production of paclitaxel in the presence of 0 (open bar), 1 mM (grayed bar), and 5 mM (filled bar) of DL-β-phenylalanine in plant cell cultures after 1, 2, 3, 4, and 5 weeks. FIG. 7B shows production of baccatin III in the presence of 0 (open bar), 1 mM (grayed bar), and 5 mM (filled bar) of DL-β-phenylalanine in plant cell cultures after 1, 2, 3, 4, and 5 weeks.

FIG. 8A shows production of paclitaxel in control cells (open bar), cells exposed to DL-β-phenylalanine (grayed bar), and cells exposed to DL-β-phenylalanine and benzoic acid (filled bar) after 2, 3, 4, and 5 weeks. FIG. 8B shows production of baccatin III in control cells (open bar), cells exposed to β-phenylalanine (grayed bar), and cells exposed to DL-β-phenylalanine and benzoic acid (filled bar) after 2, 3, 4, and 5 weeks.

FIG. 9 provides a comparison of the deduced amino acid sequence of phenylalanine aminomutase cDNA and phenylalanine ammonia-lyase from *Pinus taeda*. Identical amino acid residues are highlighted.

DETAILED DESCRIPTION OF THE INVENTION

Paclitaxel is a highly complex diterpene alkaloid consisting of a C13 side chain derived from phenylalanine and a highly modified diterpene (baccatin III). Biochemical evidence derived from feeding studies of various potential intermediates to the C13 side chain suggests the following biosynthetic scheme (also see FIG. 1). The first committed step is the conversion of α-phenylalanine to β-phenylalanine (3-amino-3-phenylpropionic acid). β-phenylalanine is then hydroxylated to form phenylisoserine, which is transferred to baccatin III at the C13 hydroxyl group (Fleming et al. J. Am. Chem. Soc. 1994 116: 4137-4138). The resulting debenzoylpaclitaxel is benzoylated to form paclitaxel (Fleming et al. J. Am. Chem. Soc. 1994 116: 4137-4138). β-phenylalanine also has been shown to be the source of the benzoic acid moiety transferred to the C13 side chain as the final enzymatic step in the synthesis of paclitaxel (Fleming et al. J. Am. Chem. Soc. 1994 116: 4137-4138).

Figure 1:
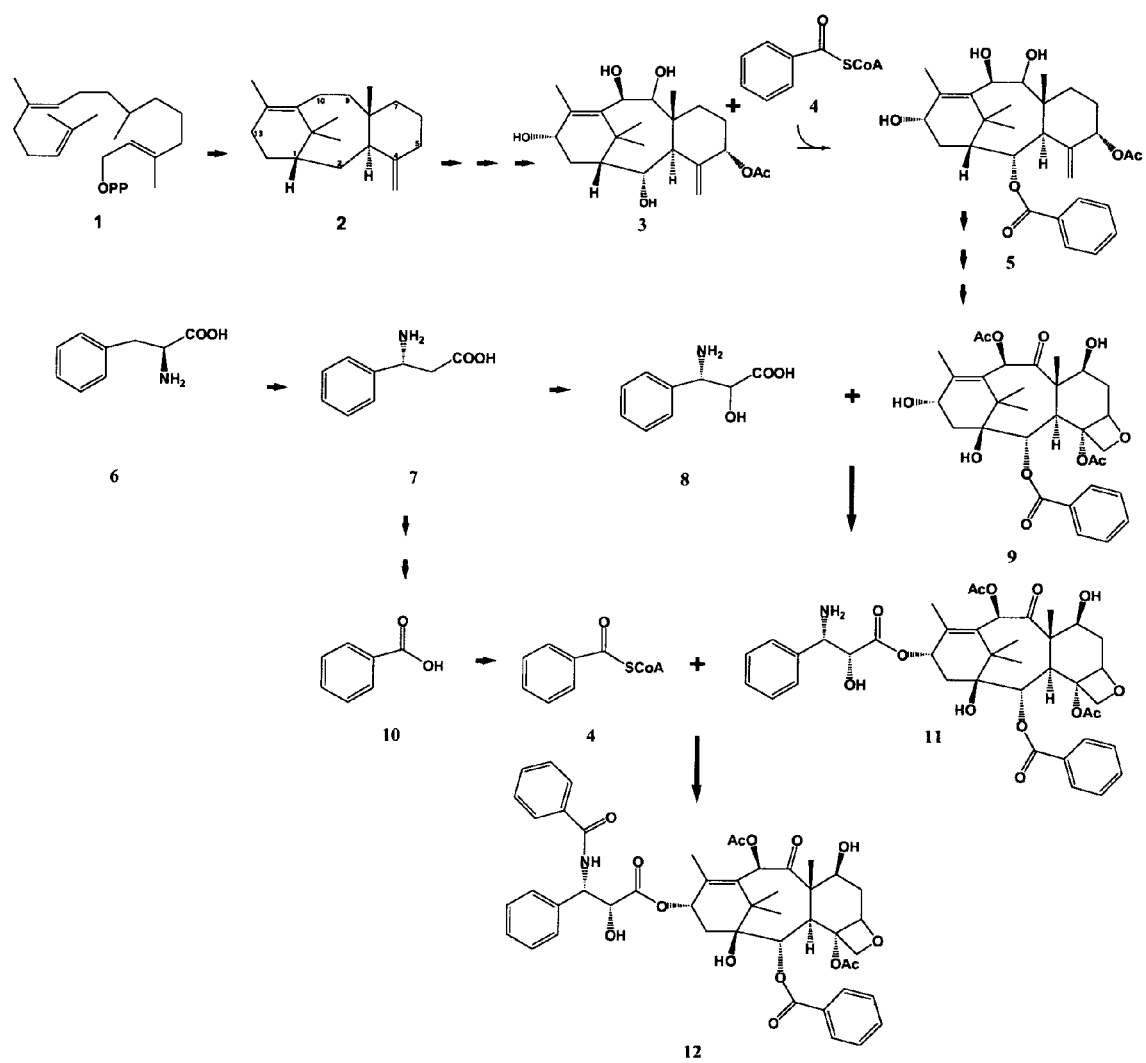
FIG. 1 provides a proposed biosynthetic scheme for paclitaxel. The chemical names of the numbered structures are as follows: 1, Geranylgeranyl diphosphate; 2, Taxadiene; 3, Taxa-4(20), 11-diene-2-α-9, 10β-13α-tetrahydroxy-5α-acetate; 4, Benzoyl CoA; 5, 9-10β-13α-Trihydroxy-5α-acetate-2α-benzoate-taxa-4(20), 11 diene; 6, α-Phenylalanine; 7, β-Phenylalanine; 8, Phenylisoserine; 9, Baccatin III; 10, benzoic acid; 11, Debenzoyl Paclitaxel; 12, Paclitaxel.

The baccatin III biosynthetic pathway begins with the ubiquitous primary metabolite geranylgeranyl diphosphate and, following 13 to 15 enzymatic steps, ends with the transacylation of 10-deacyl baccatin III to baccatin III (Fleming et al. J. Am. Chem. Soc. 1994 116: 4137-4138). As shown in FIG. 1, baccatin III is benzoylated at the C2 position, thus indicating that the biosynthesis of baccatin III requires a source of benzoic acid. Feeding studies using benzoic acid and β-phenylalanine indicate benzoic acid is derived from β-phenylalanine to be incorporated into the paclitaxel C13 side chain, thus suggesting that two pools of benzoic acid exist within the *Taxus* cell, one for the C13 side chain derived from β-phenylalanine and another for baccatin III derived from the traditional phenylalanine to cinammic acid pathway (Bjorklund and Leete, Phytochemistry 1992

31:3883). The presence of two distinct pools of benzoic acid are indicative of spatial separation between the baccatin III biosynthetic pathway and the C13 side chain/paclitaxel biosynthetic pathway.

The conversion of α-phenylalanine to β-phenylalanine by phenylalanine aminomutase being the first committed step in paclitaxel biosynthesis and β-phenylalanine being identified as the first intermediate in the side chain biosynthesis indicates that manipulation of either β-phenylalanine or phenylalanine aminomutase will have a direct impact on paclitaxel biosynthesis. The present invention enables the manipulation of taxane compositions and levels by providing a method to purify phenylalanine aminomutase to homogeneity, by isolating the phenylalanine aminomutase cDNA, and by demonstrating the addition of β-phenylalanine and/or benzoic acid to alter paclitaxel yield and ratios of paclitaxel to baccatin III. Thus, the present invention provides compositions and methods for altering the biosynthesis of taxanes such as paclitaxel and taxane-related compounds such as baccatin III and baccatin VI. In addition, the compositions of the present invention can be used in accordance with well known techniques to identify phenylalanine aminomutase genes in other species. Mutants in the phenylalanine aminomutase gene affording enzymes whose biocatalytic properties have been altered can also be generated using well known techniques. Also, common techniques using the phenylalanine aminomutase gene sequence can be employed to isolate genomic sequences adjacent to the gene, which contain the cis-acting elements that regulate gene expression.

By "phenylalanine aminomutase", it is meant an enzyme capable of catalyzing the transfer of an amino group from a 2-position of L-α-phenylalanine to form 3-amino-3-phenyl-propionic acid (β-phenylalanine).

In one aspect of the present invention, a method of purifying phenylalanine aminomutase from plant cell cultures to homogeneity is provided. Also provided is the purified phenylalanine aminomutase enzyme.

By "pure" or "purified" as used herein, it is meant that the phenylalanine aminomutase is equal to, or more preferably greater than, 95% homogeneous as determined by SDS-PAGE.

In this purification method, crude extracts from plant cells are first prepared. In a preferred embodiment, the crude extracts are prepared via suspension of frozen plant cells in potassium phosphate buffer containing dithiothreitol (DTT). The extracts are treated to remove phenolic compounds preferably via addition of XAD-4 resin (Sigma Aldrich Corp., St. Louis, Mo.) and polyvinylpyrrolidone (PVP; Sigma Aldrich Corp., St. Louis, Mo.). The extracts are then stirred at 4° C. for several hours, followed by centrifugation, preferably at 10,000×g for 2 hours, to remove cell debris and phenolic compounds. The supernatant is then concentrated, preferably to approximately 50 ml, and the concentrated fraction is dialyzed by addition of at least 200 ml of the potassium phosphate DTT containing buffer. The dialyzed fraction is concentrated by ultrafiltration to remove endogenous β-phenylalanine. Typically, the final volume of the crude extracts after the above procedure is about 40-50 ml and contains 100-150 mg of protein.

Protein is then precipitated from the crude extract preferably via addition of two separate aliquots of solid ammonium sulfate. Ammonia sulfate fractionation gives excellent yield and reasonable purification. In this procedure, a first aliquot of solid ammonium sulfate is added to 30% saturation while stirring. The solution is centrifuged, preferably at 10,000×g for 60 minutes, and the pellet is discarded. Additional solid ammonium sulfate is then added to 50% saturation while stirring. The solution is again centrifuged at 10,000×g for 60 minutes to obtain the pellet. The phenylalanine aminomutase enzyme is then purified to homogeneity by two additional steps resulting in more than 150-fold purification.

In the first of these additional steps, the pellet from the second 50% ammonium sulfate precipitation is dissolved in Tris-HCl buffer (pH 7.0) containing 1 mM DTT and 1 mM MgCl. The solution is then applied to an affinity chromatography column such as Reactive Green 19 (Sigma Aldrich Corp., St. Louis, Mo.) chromatography column (2×10 cm) comprising a dye attached to dextran equilibrated with the same buffer from which the flow-through and an additional 15 ml of the buffer wash are collected. This affinity chromatography step is essential for the purification scheme as this column separates phenylalanine aminomutase from another closely related enzyme, phenylalanine ammonia-lyase. Phenylalanine ammonia-lyase utilizes the same substrate and has a similar molecular weight. The presence of $Mg^{2+}$ is also essential to this step because phenylalanine ammonia-lyase only binds to the column in the presence of $Mg^{2+}$.

Next, the flow-through and wash fractions are combined and dialyzed by ultrafiltration to change the buffer to a Tris-HCl buffer at pH 9.0 containing 1 mM DTT and 1 mM $MgCl_2$ in a final volume of 7-8 ml.

This final volume of 7-8 ml is then applied onto a second affinity chromatography column, preferably a 10 ml (2×10 cm) column containing Heparin-Agarose Type I (Sigma Aldrich Corp., St. Louis, Mo.), equilibrated with the Tris-HCl buffer at pH 9.0 containing 1 mM DTT and 1 mM $MgCl_2$. The column is first washed with approximately 30 ml of the buffer. The enzyme is then eluted with approximately 20 ml of the buffer containing 0.1 M NaCl. The eluant can then be further concentrated. This final step gives a relatively low yield due mainly to the weak binding between phenylalanine aminomutase and Heparin-agarose. Typically binding will not occur if the buffer pH is below 9.0. Accordingly, it is preferred that the buffer has a pH of at least 9.0.

The results of a typical purification of phenylalanine aminomutase from plant cell cultures are summarized in Table 1.

TABLE 1

Purification of Phenylalanine Aminomutase (PAM)

| Step | Total Protein (mg) | Total activity (µg/h) | Specific activity (µg/h/mg) | Yield (%) | Purification (fold) |
|---|---|---|---|---|---|
| Crude extract | 123.61 | 178.0 | 1.44 | 100 | 1 |
| Ammonium sulfate | 39.60 | 161.5 | 4.08 | 90.8 | 2.8 |
| Reactive Green 19 | 2.46 | 158.8 | 64.54 | 89.2 | 44.8 |
| Heparin-agarose | 0.065 | 14.8 | 227.33 | 8.3 | 157.9 |

SDS-PAGE (sodium dodecyl sulfate-polyacrylamide gel electrophoresis) was performed to separate the proteins from each step and to demonstrate that the phenylalanine aminomutase protein was purified to homogeneity.

Characteristics of the purified phenylalanine aminomutase were then determined. The denatured molecular weight of phenylalanine aminomutase was estimated to be 80 kDa by SDS-PAGE, and the native molecular weight was determined to be 162 kDa. These results indicate that phenylalanine aminomutase is a homodimeric protein. Unlike lysine aminomutase, activity of purified phenylalanine aminomutase was not dependent upon any cofactors. Neither pyridoxyl-5-phosphate (PLP) nor S-adenosyl-L-methionine (SAM) affected the enzyme activity and the enzyme was fully functional without any cofactors. The study of substrate specificity indicated L-α-phenylalanine to be the only substrate for this enzyme. Neither D-α-phenylalanine nor any other amino acids examined were substrates for the purified phenylalanine aminomutase.

Kinetic constants for the purified phenylalanine aminomutase were also measured by standard first order kinetic model. The $K_m$ value for L-α-phenylalanine was 1.1 mM while $V_{max}$ value was 303.1 µg/minute/mg protein. Purified phenylalanine aminomutase was relatively stable at both 4° C. and room temperature.

The pH optimum of phenylalanine aminomutase was determined with sodium acetate, potassium phosphate and Tris-HCl at different pHs. The optimum pH for phenylalanine aminomutase was found to occur between 7.5 and 8.0 with either 50 mM potassium phosphate or 50 mM Tris-HCl buffer.

Sequencing of the purified phenylaminomutase was also performed. More specifically, N-terminal sequencing was performed on the whole protein as well as reverse HPLC-purified tryptic fragments using an Enhanced Hewlett-Packard G1005A amino acid sequencer (Hewlett-Packard, Palo Alto, Calif.). Each sample was analyzed for 15-20 cycles and the cycles with determinable amino acid residues are reported below in Table 2.

Uppercase letters represent highest confidence, lowercase represent reasonable confidence, lowercase letters in parentheses represent lower confidence assignments.

TABLE 2

Amino acid sequence of PAM peptides

| HPLC Fractions | Amino Acid Sequence | Peptide Name | Location in PAM | SEQ ID NO: |
|---|---|---|---|---|
| 106-108: | LLNSNVSp(m)(m) | PAM4 | 158 | 6 |
| 112-114a: | EYYSIDK | PAM5 | 307 | 7 |
| 112-114b: | LAEFEK | PAM6 | 581 | 8 |
| 119-122: | LsDRLENEMTAVR | PAM1 | 588 | 9 |
| 127-129a: | tCAs(s)VDELpatatr | PAM7 | 10 | |
| 127-129b: | (g)atr | PAM8 | Not found | 11 |
| 151-154: | VGLR | PAM2 | 216 | 12 |
| 158-161: | LNsFTYGcXGir | PAM3 | 137 | 13 |
| N-terminal | (f)FAVEAR(s)(h)V | | | 14 |

In another aspect of the present invention, isolated nucleic acid sequences encoding phenylalanine aminomutase and polypeptides encoded thereby are provided. The cDNA encoding phenylalanine aminomutase is depicted in FIG. 2, SEQ ID NO: 1. The starting methionine codon (ATG) begins at nucleotide 9, the stop codon (TAG) begins at nucleotide 2136 and the entire cDNA is 2277 nucleotides. The deduced amino acid sequence for a phenylalanine aminomutase polypeptide encoded by this nucleic acid sequence is depicted in FIG. 3, SEQ ID NO: 2. The appearance of eight of the nine peptide sequences from the purified phenylalanine aminomutase (shown in Table 2) in the deduced amino acid sequence of phenylalanine aminomutase confirms that the correct cDNA was isolated.

Searches performed using the Basic Logic Alignment Search Tool (BLAST®, NCBI, Bethesda, Md.; Altschul et al. J. Mol. Biol. 215(3)4-3-410 (1990)) indicate phenylalanine aminomutase to be related to phenylalanine ammonia-lyases. For example, a BLAST® search showed that the amino acid sequence of phenylalanine ammonia-lyase deduced from the cDNA isolated from Pinus taeda (Genbank Accession number AAA84889) is 43% identical and 68% similar to the phenylalanine aminomutase cDNA. FIG. 9 provides a comparison of these sequences that reveals at least four highly conserved amino acid regions believed to be functionally significant as well as useful in designing degenerate nucleotide PCR primers for isolating phenylalanine aminomutase from other plant species. The four regions are located at numbers 79-87, 423-428, 453-460 and 477-482 of the phenylalanine aminomutase amino acid sequence shown in FIG. 9.

Nucleic acid sequences of the genomic PCR fragment encoding phenylalanine aminomutase from three different Taxus species, namely T. chinensis, T. media and T. canadensis, are depicted in FIG. 4 (SEQ ID NO: 3), FIG. 5 (SEQ ID NO: 4) and FIG. 6 (SEQ ID NO: 5), respectively. In the nucleic acid sequence of SEQ ID NO: 3, the starting methionine codon (ATG) begins at nucleotide 63, the stop codon (TAG) begins at nucleotide 2293 and the entire fragment is 2411 nucleotides in length. The genomic fragment contains an intron that begins at nucleotide 1154 and ends at nucleotide 1312. In the nucleic acid sequence of SEQ ID NO: 4, the starting methionine codon (ATG) begins at nucleotide 1, the stop codon (TAG) begins at nucleotide 2231 and the entire fragment is 2233 nucleotides in length. The genomic fragment contains an intron that begins at nucleotide 1091 and ends at nucleotide 1260. In the nucleic acid sequence of SEQ ID NO:5, the starting methionine codon (ATG) begins at nucleotide 1, the stop codon (TAG) begins at nucleotide 2231 and the entire fragment is 2235 nucleotides in length. The genomic fragment contains an intron that begins at nucleotide 1091 and ends at nucleotide 1260.

The isolation and functional expression of a phenylalanine aminomutase cDNA was accomplished using a reverse genetics approach. Degenerate primers as depicted in Table 3 were designed from four of the nine peptides sequences generated from the purified phenylalanine aminomutase protein (see Table 2).

TABLE 3

Degenerate Primers to Selected phenylalanine aminomutase peptides

| Peptide Name | Amino Acids Used | SEQ ID NO: | Primer Sequence | SEQ ID NO: |
|---|---|---|---|---|
| PAM1 | LENEMT | 15 | YTN GAR AAY GAR ATG AC | 16 |
| PAM1.2 | LENEMTAV | 17 | YTN GAR AAY GAR ATG ACI GCI GT | 18 |
| PAM3 | LNSFTYG | 19 | YTI AAY WBI TTI CAN TAY GG | 20 |
| PAM3.1 | LNSFTYG | 21 | YTI AAY WBI TTY CAN TAY GG | 22 |
| PAM4 | LLNSNV | 23 | YTI YTI AAY WBN AAY GT | 24 |

TABLE 3-continued

Degenerate Primers to Selected phenylalanine aminomutase peptides

| Peptide Name | Amino Acids Used | SEQ ID NO: | Primer Sequence | SEQ ID NO: |
|---|---|---|---|---|
| PAM4.1 | LLNSNVS | 25 | YTI YTI AAY WBI AAY GTN CC | 26 |
| PAM5 | EYYSID | 27 | GAM TAY TAY WBN AYH GA | 28 |
| Pam5.1 | EYYSIDK | 7 | GAM TAY TAY WBN ATH GAY AA | 29 |

Following the redesign of the degenerate primers based on four of the eight peptide sequences, two DNA fragments (approximately 800 and 600 bps in length) were synthesized in a 3' RACE PCR reaction. The reaction consisted of the induced vector cDNA library as a template, the degenerate primer PAM 1.2 (designed to the internal peptide, LSDRLE-NEMTAVR (SEQ ID NO:10) and the M13F primer (5' TGACCGGCAGCAAAATG3' (SEQ ID NO:30) as the anchor. Both fragments were sequenced and shown to be 100% identical through to the poly A addition site of the 600 bp fragment with the 800 bp fragment extending 200 bp further on the 3' end, thus suggesting that the fragments are examples of the same gene using different poly(A) addition sites.

To clone the 5' end of the cDNA, a RACE (Rapid Amplification of cDNA Ends) library was synthesized using a MARATHON™ cDNA amplification kit (Clontech, Palo Alto, Calif.). The library was constructed using mRNA isolated from T. chinensis cells grown in production medium for 6 days. A 5' RACE, gene specific primer (5' TGCATC-GAACACTTTCTGCACGTCCTCT 3'; SEQ ID NO:31) was designed to the 600 bp PAM 3' RACE fragment. The resulting PCR amplicon was 2.2 kb in length and was subcloned into PCR-Script™ (Stratagene, La Jolla, Calif.). The full length cDNA was isolated with a 5' specific primer pam93mut, TCCTTGCTCTCATATTATGGGGTTTGC (SEQ ID NO:32), that created a NdeI restriction site at the starting ATG and a 3' specific primer pam2350mutc, GGGATCCTTTTAAAACAAAAATTAATTAGGGTT (SEQ ID NO: 33) that created a BamHI site and included 227 nucleotide of the 3' untranslated region. The resulting full length phenylalanine aminomutase cDNA was subcloned into PCR-Script™ (Stratagene, La Jolla, Calif.) and sequenced. This sequence is depicted in FIG. 2. A NdeI BamHI restriction digest phenylalanine aminomutase DNA fragment was subcloned into the pBMS2000 E. coli protein expression vector (described in U.S. Pat. No. 6,068,991, the teachings of which are herein incorporated by reference in their entirety) and then transformed into E. coli strain Epicurian coli® XL1-Blue (Stratagene, La Jolla, Calif.). Following expression and enzymatic assay, the functional enzyme synthesized an average of 588 ng β-phenylalanine per mg of E. coli protein. This functional expression demonstrates conclusively that the cDNA to phenylalanine aminomutase has been amplified and cloned.

The genomic DNA as depicted in FIG. 4, SEQ ID NO:3, was generated using PCR containing gene specific primers PAM5F2, TCAGTTTTATCTCGCTCAAGT (SEQ ID NO:34), and PAM3R, TACAGTCGCTTCTGCGGAAT (SEQ ID NO:35), designed to the 5' and 3' untranslated regions of the phenylalanine aminomutase cDNA and genomic DNA isolated from Taxus chinensis cell line P97-1 cell cultures. The genomic PCR product was sequenced directly from the reaction. Therefore the sequence is considered a consensus phenylalanine aminomutase sequence since the product contains a small percentage of sequence heterogeneity caused by slight differences found between even allelic genes. The cloned cDNA and the genomic PCR product are 99.8% identical on the nucleotide level and 99.7% identical on the amino acid level (see Table 4).

The genomic PCR products from two other Taxus species, T. media and T. canadensis were synthesized and sequenced in a similar manner. In order to ensure that the PCR reactions would generate specific products, the 5' primer pam63, ATGGGGTTTGCCGTGGAATCG (SEQ ID NO:36), and the 3' primer pam2137c, CTAGACGCCGTTGGCGCA (SEQ ID NO:37), were designed to start and end with the beginning and ending of the coding region of phenylalanine aminomutase. The T. media sequence is depicted in FIG. 5, SEQ ID NO:4, and the T. canadensis sequence is depicted in FIG. 6, SEQ ID NO: 5. Both sequences contain an intron beginning at nucleotide 1092 and ending at nucleotide 1260.

All three phenylalanine aminomutase sequences are highly conserved. The T. chinensis is 98.6% identical to T. media and 98.7% identical to T. canadensis on the nucleotide level. The differences that result in changes in amino acids are presented in Table 4.

TABLE 4

Amino Acid Differences Identified in Phenylalanine Aminomutase cDNA and genomic PCR fragments

| | Sequences | | | | | Sequences | | | | |
|---|---|---|---|---|---|---|---|---|---|---|
| | I | II | III | IV | Location | I | II | III | IV | Location |
| Amino Acid | A | A | T | T | 20 | E | E | D | E | 303 |
| Amino Acid | R | Q | Q | Q | 96 | E | E | D | D | 473 |
| Amino Acid | P | S | S | S | 119 | C | C | C | S | 545 |
| Amino Acid | A | A | V | V | 128 | T | T | S | S | 562 |
| Amino Acid | V | V | L | L | 239 | E | E | D | D | 644 |

I = PAM T. chinensis cDNA
II = PAM T. chinensis genomic
III = PAM T. media genomic
IV = PAM T. canadensis genomic Due to degeneracy of the genetic code, nucleic acid sequences of the present invention may also comprise different nucleic acid sequences to those depicted in FIGS. 2, 4 and 5 encoding the same phenylalanine aminomutase enzyme. Nucleic acid sequences of the present invention are also inclusive of polynucleotides which hybridize under stringent conditions to the above-described nucleic acid sequences. As used herein, the term "stringent conditions"

means at least 60%, more preferably at least 80%, homology at hybridization conditions of 60° C. at 2×SSC buffer. More preferred are isolated nucleic acid molecules capable of hybridizing to the nucleic acid sequence set forth in FIG. 2, 4 or 5, or to the complementary sequence of the nucleic acid sequence set forth in FIG. 2, 4 or 5, under hybridization conditions of 3×SSC at 65° C. for 16 hours, and which are capable of remaining hybridized to the nucleic acid sequence set forth in FIG. 2, 4 or 5, or to the complementary sequence of the nucleic acid sequence set forth in FIG. 2, 4 or 5, under wash conditions of 0.5×SSC, 55° C. for 30 minutes. Nucleic acid sequences of the present invention may also comprise fragments, and derivative or variant nucleic acid sequences encoding derivatives, variants or active fragments of this enzyme. The term "variant" is inclusive of naturally occurring variants such as allelic variants, as well as mutants prepared by well-known mutagenesis techniques. With respect to variant or derivative nucleic acid sequences, differences are generally limited so that the polypeptide encoded by the nucleic acid sequence exhibits similar activity to the phenylalanine aminomutase enzyme. By "similar activity" for purposes of the present invention, it is meant that the variant enzyme is still capable of catalyzing the transfer of an amino group from the 2-position of L-α-phenylalanine to form 3-amino-3-phenylpropionic acid. Thus, changes in the nucleic acid sequences of a variant or derivative of the present invention may be silent. That is, they may not alter the amino acids encoded by the nucleic acid sequences. Alternatively, changes in the nucleic acid sequence may alter the amino acid sequence as compared to that of the phenylalanine aminomutase enzyme. Such changes may comprise amino acid substitutions, additions, deletions, fusions and truncations as compared to the amino acid sequence of the phenylalanine aminomutase enzyme. By "fragment" it is meant a nucleic acid sequence or polypeptide encoded thereby which comprises less nucleotides or amino acids than depicted in SEQ ID NO: 1, 3, 4 or 5, or 2, respectively. Preferred fragments, variants and derivatives of the present invention, when referring to the nucleic acid sequences, are those that encode polypeptides that retain essentially the same biological function as the phenylalanine aminomutase enzyme. Preferred fragments, variants and derivatives of the present invention, when referring to polypeptides, are those, which retain essentially the same biological function as the phenylalanine aminomutase enzyme. Such preferred fragments can be identified via assays measuring enzymatic catalyzation of the transfer of an amino group from a 2-position of L-α-phenylalanine to form 3-amino-3-phenylpropionic acid.

In addition to being useful in the production of phenylalanine aminomutase enzymes, the nucleic acid sequences of the present invention are also useful in isolation of genomic sequences adjacent to the phenylalanine aminomutase enzyme, as hybridization probes to isolate phenylalanine aminomutase genes or genes similar thereto in other species, and in the identification of mutations that alter the biocatalytic properties of enzymes encoded thereby.

For example, regulatory genomic sequences adjacent to a phenylalanine aminomutase gene can be identified using well known techniques to identify an isolated nucleic acid sequence of the present invention in a gene and to isolate a genomic sequence adjacent thereto. These sequences contain the cis-acting elements that regulate gene expression. Thus, isolation of such sequences may be useful in identifying modulators of expression of the phenylalanine aminomutase gene.

Nucleic acid sequences of the present invention, particularly fragments thereof can also serve as hybridization probes useful in the identification and isolation of phenylalanine aminomutase genes or genes similar thereto in other species. Production and use of such probes is performed routinely in accordance with teachings provided herein and in accordance with well known techniques.

The nucleic acid sequences of the present invention can also be used to identify mutant phenylalanine aminomutase genes encoding proteins with biocatalytic properties altered as compared to a wild-type phenylalanine aminomutase enzyme. In this aspect of the present invention, an isolated nucleic acid sequence encoding a wild type phenylalanine aminomutase such as the nucleic acid sequence depicted in FIG. 2, 4 or 5 is mutated in accordance with well known, standard techniques. A polypeptide encoded by the mutant isolated nucleic acid sequence is then expressed and one or more biocatalytic properties of the expressed polypeptide are assessed. Examples of biocatalytic properties of the polypeptide which can be determined include, but are not limited to substrate specificity, Km, turnover rate, pH optimum, temperature optimum and solvent environment. One or more biocatalytic properties of the expressed polypeptide are then compared with the same biocatalytic property or properties of a wild-type phenylalanine aminomutase to identify any mutations to the nucleic acid sequences resulting in polypeptides with biocatalytic activities different from wild-type phenylalanine aminomutase.

Various examples of plants cells are known wherein increased gene expression to increase a biosynthetic enzyme level results in an overall increase in a particular secondary metabolite. For example, alfalfa plants respond to wounding by synthesizing large amounts of an isoflavonoid phytoalexin. Since this biosynthetic pathway requires 8 to 12 enzymes, it is similar to paclitaxel whose pathway requires 12 to 14 enzymes. By increasing expression of methyltransferase, significant increases in phytoalexin were demonstrated (He, X. Z. and Dixon, R. A. The Plant Cell 2000 12(9):1689-1702). In addition, an increase in yield of monoterpenes occurs in mint when a reductoisomerase from the biosynthetic pathway is genetically overexpressed (Mahmoud, S. S. and Croteau, R. B. Proc. Natl Acad. Sci. USA 2001 98:8915-8920). Interestingly, Mahmoud and Croteau also show that the composition of the monoterpenes may be altered when a gene is genetically manipulated so that underexpression occurs. Overexpression of phenylalanine aminomutase is expected to increase paclitaxel titer and increase the paclitaxel to baccatin III ratio, a desired outcome in downstream processing, in similar fashion. In contrast, a significant decrease in phenylalanine aminomutase expression is expected to reduce paclitaxel levels and increase baccatins including, but not limited to, baccatin III and baccatin VI.

In embodiments wherein a nucleic acid sequence encoding the phenylalanine aminomutase enzyme is added to the plant cells, it is preferred that this be performed via genetic transformation with a vector comprising the nucleic acid sequence. The enzyme can be overexpressed in host cells transformed with a vector comprising a nucleic acid sequence of the present invention. For example, Example 4 of the instant application sets forth a method for transforming E. coli with a vector comprising a nucleic acid sequence of the present invention and expressing phenylalanine aminomutase in this host cell. However, the substrate for phenylalanine aminomutase, L-α-phenylalanine, is ubiquitous in all living creatures. Accordingly, the phenylalanine aminomutase gene may be expressed in almost any yeast, bacterial or mammalian host cell.

Thus, additional aspects of the present invention relate to vectors comprising a nucleic acid sequence encoding phenylalanine aminomutase as well as host cells comprising these vectors and expressing phenylalanine aminomutase.

Another aspect of the present invention relates to methods for altering production of taxanes and taxane-related compounds by biosynthesis, which comprises supplementing production medium with β-phenylalanine and/or benzoic acid or a salt thereof. Further, supplementing production medium with β-phenylalanine and/or benzoic acid or a salt thereof increases the ratio of taxanes produced as compared to taxane-related compounds.

Enhanced productivity of paclitaxel was observed in batch cultivation of *T. chinensis* cells upon addition of 1 mM DL-β-phenylalanine. Further, in only the second week of cultivation, baccatin III titer in the control showed a marked difference from the 5 mM DL-β-phenylalanine batch. Results from these experiments are depicted in FIG. 7. In the presence of 5 mM DL-β-phenylalanine, a 40% increase of paclitaxel (see FIG. 7A) and an 80% reduction of baccatin III were observed at the end of the second week (see FIG. 7B). However, the increase in paclitaxel production decreased in subsequent weeks and was no longer significantly increased as compared to the control at the end of the fifth week. These results indicate that 5 mM DL-β-phenylalanine enables rapid conversion of baccatin III to paclitaxel in a short period. Cells cultured in medium supplemented with 1 mM DL-β-phenylalanine consistently showed enhancement of paclitaxel production and produced 26% more paclitaxel than the controls (192 units/L vs. control 152 units/L) at the end of the fifth week.

Figure 8:
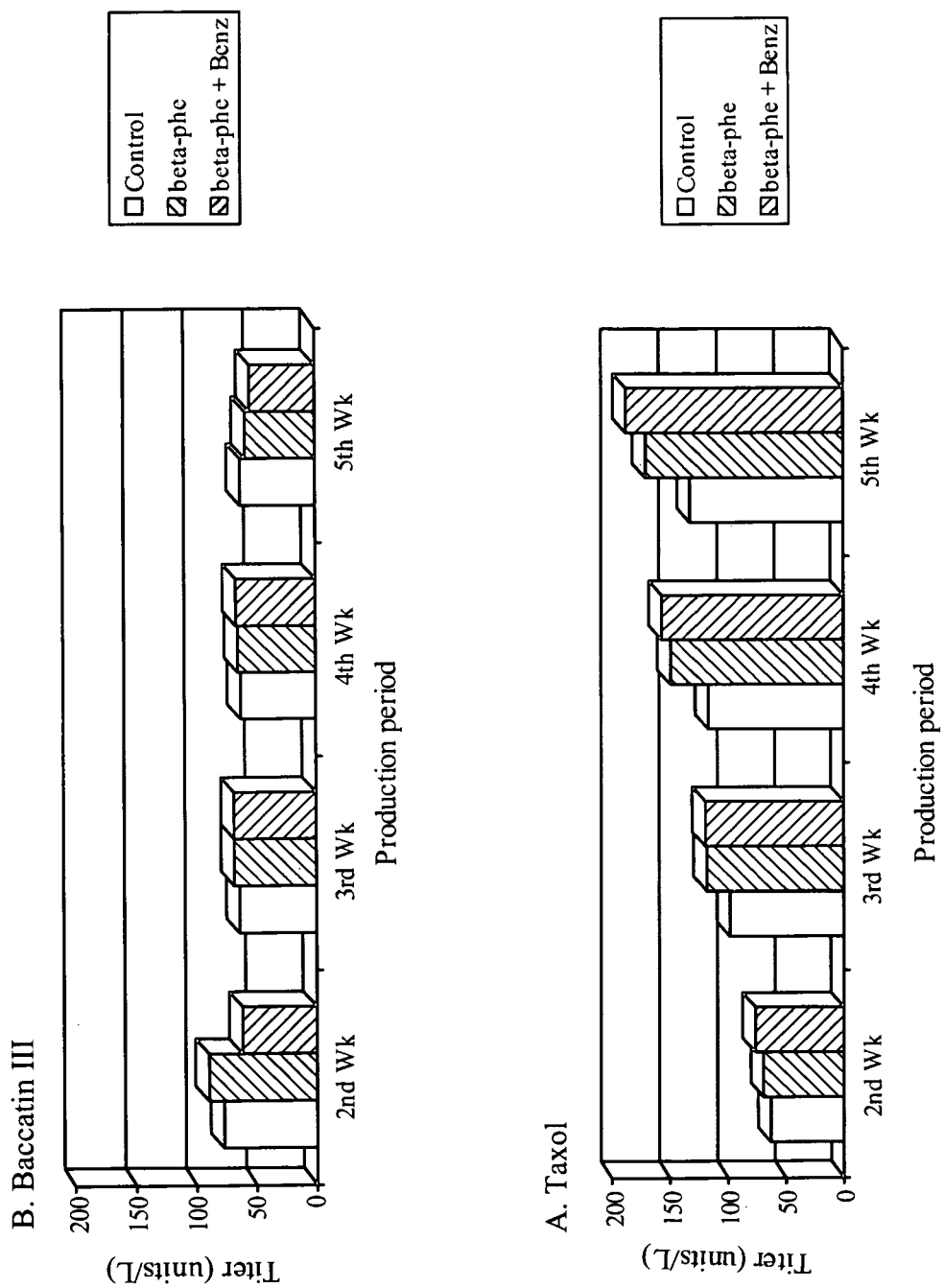
FIG. 8 is a bargraph showing the effects of DL-β-phenylalanine (DL-3-amino-3-phenylpropionic acid) and benzoic acid on paclitaxel and baccatin III production in fed-batch cultivation of *T. chinensis* cells. Each value represents the average of six samples.

Enhanced paclitaxel production was also observed in fed-batch cultivation *T. chinensis* cells with feeding of DL-β-phenylalanine and benzoic acid. Results from these experiments are depicted in FIG. 8. In the presence of 2.2 mM DL-β-phenylalanine, the cells produced 29% more paclitaxel (171 units/L vs. control 132 units/L) than the control at the end of the fifth week (see FIG. 8A). Feeding with a mixture of DL-β-phenylalanine and benzoic acid further enhanced paclitaxel productivity during fed-batch cultivation to 43% (189 units/L vs. control 132 units/L) at the end of the fifth week (see FIG. 8A). While a decrease in baccatin III titers was not observed in any of the fed-batch cultivations, the ratio of paclitaxel to baccatin III of cells cultivated in medium supplemented with DL-β-phenylalanine alone (2.9) or in combination with benzoic acid (3.6) was higher than controls (2.2) (see FIG. 8B).

These results indicate that both β-phenylalanine and benzoic acid enhanced paclitaxel production in *T. chinensis* cell cultures. Accordingly, supplementing the production medium of plant cell cultures with β-phenylalanine alone or benzoic acid or a salt thereof alone, or more preferably a combination of β-phenylalanine and benzoic acid or a salt thereof, provides a useful means for enhancing production of taxanes such as paclitaxel.

The following nonlimiting examples are provided to further illustrate the present invention.

EXAMPLES

Example 1

Phenylalanine aminomutase Protein Isolation and Characterization

Enzyme Assay and HPLC Method

The standard PAM activity assay mixture contains 5 mM L-α-phenylalanine, 1 to 10 μg enzyme in 50 mM Tris-HCl buffer (pH 7.5) in a final volume of 0.5 ml. Enzyme reactions were carried out at 28° C., 150 rpm for 18 hours and terminated by addition of 50 μl ethanol to precipitate proteins. After centrifugation for 5 minutes, the supernatants were analyzed by a reverse phase HPLC method. The formation of β-phenylalanine was quantified based on peak area compared to the β-phenylalanine standard curve. Enzyme activity is expressed as μg β-phenylalanine formed per hour per mg protein. HPLC analysis used a YMC Ph column (4.6×150 mm; Waters, Milford, Mass.), and a flow rate of 1.2 ml/minutes. Absorbance was monitored at 210 nm. The method employed two solvents A, water; and B, $CH_3CN$ and a gradient consisting 0% to 12% B for 6 minutes, 12% to 90% in 1 minute and returning to 0% in 1 minute. Retention times of L-α-phenylalanine and β-phenylalanine are 4.3 minutes and 3.5 minutes, respectively.

Protein Assay

Protein concentrations were determined using a propositional protein binding dye method and microassay kit purchased from Bio-Rad Laboratories (Hercules, Calif.).

Enzyme Purification

To prepare the crude extracts, 100 grams (wet weight) of frozen plant cells were suspended in 500 ml of cold 50 mM potassium phosphate buffer (pH 7.5) containing 1 mM dithiothreitol (DTT). After addition of 50 grams of the nonionic polymeric adsorbent XAD-4 resin (Sigma Aldrich Corp., St. Louis, Mo.) and 50 g PVP, the extracts were stirred at 4° C. for 2 hours, then centrifuged at 10,000×g for 2 hours. The supernatant was concentrated to approximately 50 ml by an ultrafiltration concentrator with a PM-30 membrane (Amicon, Inc. Beverly, Mass.), and the concentrated fraction was further dialyzed by addition of at least 200 ml of the buffer and concentrated by ultrafiltration to remove endogenous β-phenylalanine. Typically, the final volume of the crude extracts after above procedures is about 40-50 ml containing 100-150 mg of protein.

Solid ammonium sulfate was added to the crude extracts to 30% saturation while stirring. The solution was centrifuged at 10,000×g for 60 minutes and the pellet was discarded. Additional solid ammonium sulfate was added to 50% saturation while stirring. The solution was then centrifuged at 10,000×g for 60 minutes to obtain the pellet.

The pellet from 50% ammonium sulfate precipitation was dissolved in 15 ml of 10 mM Tris-HCl buffer (pH 7.0) containing 1 mM DTT and 1 mM $MgCl_2$. The dissolved pellet was then applied onto a 10 ml Reactive Green 19 (Sigma Aldrich Corp., St. Louis, Mo.) chromatography column (2×10 cm) comprising this green dye attached to dextran equilibrated with 10 mM Tris-HCl buffer (pH 7.0) containing 1 mM DTT and 1 mM $MgCl_2$, and the flow-through and an additional 15 ml of the buffer wash were collected. The flow-through and wash fractions were combined and dialyzed by ultrafiltration to change the buffer to 10 mM Tris-HCl buffer (pH 9.0) containing 1 mM DTT and 1 mM $MgCl_2$ in final volume of 7 to 8 ml.

The active fraction was then applied onto a 10 ml Heparin-Agarose Type I (Sigma Aldrich Corp., St. Louis, Mo.) column (2×10 cm) equilibrated with 10 mM Tris-HCl buffer (pH 9.0) containing 1 mM DTT and 1 mM $MgCl_2$. The column was washed with 30 ml of the buffer and the enzyme was eluted with 20 ml of the buffer containing 0.1 M NaCl. The eluant was then concentrated to small volume.

SDS-PAGE

Sodium dodecyl sulfate-polyacrylamide gel electrophoresis (SDS-PAGE) was performed with the 10% ready gels from Bio-Rad (Hercules, Calif.). The gels were stained with Coomassie blue. Broad range protein standards from Bio- Rad (Hercules, Calif.) were used to estimate denatured molecular weight of the enzyme.

Determination of Native Molecular Weight

Size exclusion chromatography was performed using a 100 ml column of Sephacryl S-200 HR (Sigma Aldrich Corp., St. Louis, Mo.)) gel filtration column (2.5×35 cm) equilibrated with 10 mM potassium phosphate buffer (pH 7.0) containing 1 mM DTT. Enzyme samples and 0.25 ml of molecular weight standards (670 kDa, 158 kDa, 44 kDa, 17 kDa and 1.35 kDa) from Bio-Rad (Hercules, Calif.) were applied onto the column. The column was eluted with the buffer at 1 ml/minute by collecting every 4 mls as a fraction monitored at 280 nm. The native molecular weight of the enzyme was calculated by comparing the elution volume to the standard curve.

Other Determinations

Purified enzyme preparations were used to determine the properties of the enzyme including cofactor requirements, substrate specificity, kinetic constants, thermostability and pH optima. For the determination of cofactor requirements, 1 mM pyrodoxal 5'-phosphate (PLP) or S-adenosyl-L-methionine (SAM) was included in the standard reaction mixtures and the formation of β-phenylalanine was analyzed by HPLC. To determine substrate specificity, a variety of amino acids in both L- and D- including, but not limited to lysine, tyrosine, tryptophan, and histidine, were used at 5 mM as substitutes for L-α-phenylalanine in the standard reaction mixtures. For the determination of kinetic constants, L-α-phenylalanine concentration in the reaction mixture was varied in the range of 0.156 mM to 15 mM for measuring enzyme activity. Thermostability and pH optima were conducted by incubating the enzyme reaction mixtures at different temperatures or in different buffers with varying pHs.

Phenylalanine Aminomutase Peptide Mapping

Purified phenylalanine aminomutase protein was run on a SDS-PAGE gel, blotted onto PVDF (polyvinylidene difluoride) membrane (Bio-Rad, Hercules, Calif.), and the approximately 80 kDa band excised. All protein analysis effort was done in accordance with Hewlett-Packard (Palo Alto, Calif.) sequencing protocols (Miller C. G., Adsorptive Biphasic Column Technology for Protein Sequence Analysis and Protein Chemical Modification. Methods: A Companion to Methods in Enzymology (Academic Press), Vol. 6, No. 3, September 1994, pp. 315-333). The PVDF-bound sample (approximately 4 μg) and PVDF control sample were subjected to alkylation using a Hewlett-Packard Protein Chemistry station. The PVDF strips were treated at 50° C. under an argon atmosphere with 10 mM dithiothreitol in 6 M guanidine at pH 8.3 followed by alkylation with 2 M acrylamide dissolved in the same solvent. Strips were then placed into a solution containing 100 ng of modified porcine trypsin (Promega, Madison, Wis.), 1% hydrogenated Triton X-100, 10% acetonitrile, 20 mM ammonium bicarbonate, and 5 mM ammonium carbonate (pH 8). Following a 4 hour incubation at 40° C., an additional 100 ng of trypsin was added to each mixture and the incubations continued for a total of 12 hours. The solutions were then loaded onto Perisorb RP-18 columns (EM Science, Hawthorne, N.Y.), which were subsequently washed with 1 ml of 2% trifluoroacetic acid (TFA) prior to the HPLC analysis.

Example 2

Isolation of the phenylalanine aminomutase cDNA

RNA Isolation

RNA was extracted from *Taxus* cells grown in either growth media (controls) or production media (induced) for 6 days. Total RNA isolation was performed using a RNA isolation kit from Qiagen, Inc. (Valencia, Calif.) according to the manufacturer's instructions with two modifications. The extraction buffer volume was increased two-fold to maintain the weight of tissue to buffer volume ratio suggested by the manufacturer. A 10% ethanol precipitation as taught by Levinsohn et al. (Plant Mol. Bio. Rep. 1994 12(1):20-25 ) was incorporated to remove contaminating polysaccharides. Poly A RNA was isolated using latex beads from Qiagen Inc. (Valencia, Calif.) according the manufacturer's instructions.

Vector cDNA Library Construction, Phage DNA Isolation and RACE (Rapid Amplification of cDNA Ends) cDNA Library Construction The vector cDNA was synthesized with 5 μg of induced mRNA using a cDNA synthesis kit from Stratagene (La Jolla, Calif.) following the manufacturer's instructions. Bacteriophage DNA containing the *Taxus* cDNA was isolated from contaminating *E. coli* DNA using a protocol described by Ausubel et al. (Current protocols of molecular biology. Current protocols 1987 Vol. 1: 1.13.7). The RACE library was constructed with 1 μg of induced poly A RNA using the MARATHON™ cDNA amplification kit (Clontech, Palo Alto, Calif.) according to the manufacturer's protocol.

PCR Protocols and DNA Sequencing

PCR reactions were performed using Taq DNA polymerase (Stratagene, La Jolla, Calif.) according to the manufacturer's instructions. PCR reaction using the RACE library was performed with the ADVANTAGE™ 2 PCR kit (Clontech, Palo Alto, Calif.) in accordance with the manufacturer's instructions. DNA sequencing was performed using the ABI PRISM® Big Dye™ terminator cycle sequencing kit (Applied Biosystem, Foster City, Calif.) according to the manufacturer's instructions.

Example 3

Paclitaxel Biosynthesis Enhancement by Supplementing Production Medium with DL-β-phenylalanine and benzoic acid Vegetative cells of *T. chinensis* cell cultures were inoculated into production medium at cell density of 200 grams/L. The following two cultivation procedures were used.

The first cultivation procedure was a batch cultivation using 1 or 5 mM DL-β-phenylalanine treatments in TAXOL production medium, which contains Medium N plus α-naphthaleneacetic acid, 3,4-(methylenedioxy)cinnamic acid, methyl jasmonate, and silver thiosulfate (WO97/44476). Production medium without the addition of DL-β-phenylalanine served as a control. Samples were collected weekly for analysis via high pressure liquid chromatography (HPLC) for five weeks.

The second cultivation procedure was a fed-batch cultivation, which initially used a batch medium containing 1.2× strength Medium N lacking glutamine plus 3,4-(methylenedioxy)cinnamic acid and silver thiosulfate (WO97/44476). Methyl jasmonate, α-naphthalene acetic acid, glutamine, and DL-β-phenylalanine were then fed from day 3 to day 35. Feedings were performed every three to four-days with a feeding rate equivalent to 5 mL/L/day. The total amount of DL-β-phenylalanine fed was 2.2 mmol/L during the 5 week production period. The fed-batch cultivation using a feeding solution lacking DL-β-phenylalanine was used as control. A second fed-batch cultivation treatment using DL-β-phenylalanine and benzoic acid was also performed. The total amount of both DL-β-phenylalanine and benzoic acid fed to the broth was 2.2 mmol/L during the 5-week production period. Samples were taken for HPLC assay at the end of weeks 2, 3, 4, and 5.

Example 4

Expression of phenylalanine aminomutase in *E. coli* Expression

To express phenylalanine aminomutase in *E. coli*, the cDNA (SEQ ID NO:1) was subcloned into pBMS2000 protein expression vector and transformed into Epicurian *coli*® XL-1 blue cells (Stratagene, La Jolla, Calif.). Following confirmation of proper cloning via digestion with Nde I and BamH I, the plasmid was named pPAM2000 and the protein expression of the phenylalanine aminomutase cDNA was begun.

Cultures of XL1-Blue cells containing either pPAM2000 or pBMS2000 were grown overnight and used to inoculate fresh cultures of LB media and grown at 30° C. When the cultures reach an optical density of 0.5-1.0, they were induced to synthesize the phenylalanine aminomutase protein by the addition of 100 μM IPTG (isopropylthio-β-galactoside). The bacteria were collected by centrifugation at 5000×g for 10 minutes, washed in assay buffer (50 mM Tris pH 7.5), and resuspended in assay buffer. The bacteria were lysed by sonication (2×20 pulses on ice). The enzyme was assayed by addition of L-α-phenylalanine. Samples were incubated at 18° C. overnight and the reactions were terminated by addition of ethanol. The samples were clarified by centrifugation at 16,000 g for 10 minutes. The supernatant was transferred to HPLC vials and analyzed for L-β-phenylalanine production. The HPLC method used a μBONDAPAK™ C18 column (Millipore, Milford, Mass.) and a reverse phase water (A) to acetylnitrile (B) gradient of 0 to 20% B in one minute, 20 to 30% B in 6 minutes and 30 to 90% B in one minute. L-αphenylalanine eluted at 5.2 minutes and L-β-phenylalanine eluted at 4.9 minutes. In two experiments, the recombinant PAM produced 694 and 483 ng of β-phenylalanine/mg *E. coli* protein and the pBMS2000 containing *E. coli* extracts failed to synthesize any detectable amounts of β-phenylalanine.

What is claimed is:

1. A method for altering biosynthesis of taxane in a *Taxus* species cell culture comprising altering the level and activity of phenylalanine aminomutase by transforming a *Taxus* cell with a DNA of SEQ ID NOs: 1, 3 or 5.

2. The method of claim 1 wherein the level of phenylalanine aminomutase is increased by transforming a *Taxus* cell with a DNA of SEQ ID NOs: 1, 3 or 5.

* * * * *

SEQUENCE LISTING

```
<160> NUMBER OF SEQ ID NOS: 37

<210> SEQ ID NO 1
<211> LENGTH: 2277
<212> TYPE: DNA
<213> ORGANISM: Taxus chinensis
<220> FEATURE:
<221> NAME/KEY: CDS
<222> LOCATION: (9)..(2069)

<400> SEQUENCE: 1 gctctcat atg ggg ttt gcc gtg gaa tcg cgt tct cac gta aag gat ata        50
         Met Gly Phe Ala Val Glu Ser Arg Ser His Val Lys Asp Ile
         1               5                  10 ttg ggg ctg atc aac gcg ttc aac gag gtg aag aaa att aca gta gac        98
Leu Gly Leu Ile Asn Ala Phe Asn Glu Val Lys Lys Ile Thr Val Asp
15                  20                  25                  30 ggt acg acc ccc atc acg gtg gcc cat gtc gcg gcg ctg gcc cgg agg       146
Gly Thr Thr Pro Ile Thr Val Ala His Val Ala Ala Leu Ala Arg Arg
                35                  40                  45 cat gac gtg aag gtt gcg ttg gag gcg gag caa tgc aga gcc cgt gtg       194
His Asp Val Lys Val Ala Leu Glu Ala Glu Gln Cys Arg Ala Arg Val
            50                  55                  60 gaa acc tgc tct tcg tgg gtg cag cgc aag gcg gaa gac ggc gcc gac       242
Glu Thr Cys Ser Ser Trp Val Gln Arg Lys Ala Glu Asp Gly Ala Asp
65                  70                  75 ata tac ggc gtc acc acg ggc ttc ggc gcg tgc tcg agc cgg agg acc       290
Ile Tyr Gly Val Thr Thr Gly Phe Gly Ala Cys Ser Ser Arg Arg Thr
80                  85                  90 aac cgg ctg agc gag ctg cag gag tcg ctc ata cgc tgc ctg ctc gcg       338
Asn Arg Leu Ser Glu Leu Gln Glu Ser Leu Ile Arg Cys Leu Leu Ala
95                 100                 105                 110 ggg gtg ttt act aaa gga tgc gct ccc tcc gtc gac gag ctc ccc gcg       386
Gly Val Phe Thr Lys Gly Cys Ala Pro Ser Val Asp Glu Leu Pro Ala
                115                 120                 125 acc gcc acc cgc agc gcc atg ctg ctc cgc ctt aat agt ttt acc tat       434
Thr Ala Thr Arg Ser Ala Met Leu Leu Arg Leu Asn Ser Phe Thr Tyr
            130                 135                 140
```

```
gga tgt tcc ggc atc cgg tgg gag gtc atg gaa gcg ctg gaa aag ctt         482
Gly Cys Ser Gly Ile Arg Trp Glu Val Met Glu Ala Leu Glu Lys Leu
            145                 150                 155 ctc aac agc aat gtc tct cct aaa gtg cct ctc cgg ggt tct gtg agc         530
Leu Asn Ser Asn Val Ser Pro Lys Val Pro Leu Arg Gly Ser Val Ser
        160                 165                 170 gct tcg gga gac ctc atc ccg ctc gcc tac att gca ggg ctc ctg atc         578
Ala Ser Gly Asp Leu Ile Pro Leu Ala Tyr Ile Ala Gly Leu Leu Ile
175                 180                 185                 190 ggg aag cct agc gta atc gct cgc ata ggc gac gat gtc gag gtc cct         626
Gly Lys Pro Ser Val Ile Ala Arg Ile Gly Asp Asp Val Glu Val Pro
                195                 200                 205 gcg ccc gag gcg ttg agc agg gtg ggg ctt cgg cca ttc aag ctc cag         674
Ala Pro Glu Ala Leu Ser Arg Val Gly Leu Arg Pro Phe Lys Leu Gln
            210                 215                 220 gcc aaa gaa ggg ctg gcg ctc gtc aac ggc acc tcc ttc gcc acc gcg         722
Ala Lys Glu Gly Leu Ala Leu Val Asn Gly Thr Ser Phe Ala Thr Ala
        225                 230                 235 gtc gcc tcc acc gtc atg tac gac gcc aat gtt ctg ttg ctc ctc gtc         770
Val Ala Ser Thr Val Met Tyr Asp Ala Asn Val Leu Leu Leu Leu Val
240                 245                 250 gaa acg ctt tgc gga atg ttc tgc gag gtg atc ttt gga agg gag gag         818
Glu Thr Leu Cys Gly Met Phe Cys Glu Val Ile Phe Gly Arg Glu Glu
255                 260                 265                 270 ttc gcg cat ccg ctg atc cat aaa gtg aag ccg cac ccg ggc cag atc         866
Phe Ala His Pro Leu Ile His Lys Val Lys Pro His Pro Gly Gln Ile
            275                 280                 285 gaa tcg gcg gag ctg ctc gag tgg ctg ctg cgg tcg agc ccg ttt cag         914
Glu Ser Ala Glu Leu Leu Glu Trp Leu Leu Arg Ser Ser Pro Phe Gln
        290                 295                 300 gag ctg tcg agg gag tat tac agt att gat aag ctg aag aaa ccg aaa         962
Glu Leu Ser Arg Glu Tyr Tyr Ser Ile Asp Lys Leu Lys Lys Pro Lys
305                 310                 315 cag gat cgc tat gct ctg agg tcg agc ccg cag tgg ttg gct cct ctg        1010
Gln Asp Arg Tyr Ala Leu Arg Ser Ser Pro Gln Trp Leu Ala Pro Leu
320                 325                 330 gtg cag aca atc aga gac gcc acc act aca gtg gag acg gag gtc aat        1058
Val Gln Thr Ile Arg Asp Ala Thr Thr Thr Val Glu Thr Glu Val Asn
335                 340                 345                 350 tcc gcc aat gat aac ccc atc att gac cac gcc aat gac agg gct ctc        1106
Ser Ala Asn Asp Asn Pro Ile Ile Asp His Ala Asn Asp Arg Ala Leu
            355                 360                 365 cat ggt gcg aat ttc cag ggc agc gcc gtc ggt ttc tac atg gac tac        1154
His Gly Ala Asn Phe Gln Gly Ser Ala Val Gly Phe Tyr Met Asp Tyr
        370                 375                 380 gtg cgc atc gca gta gcc ggg ctg ggg aaa ctc ttg ttc gct cag ttc        1202
Val Arg Ile Ala Val Ala Gly Leu Gly Lys Leu Leu Phe Ala Gln Phe
                385                 390                 395 acg gag ctg atg atc gaa tat tac agc aac ggc cta ccg ggg aac ctc        1250
Thr Glu Leu Met Ile Glu Tyr Tyr Ser Asn Gly Leu Pro Gly Asn Leu
            400                 405                 410 tcc ctg ggg ccg gac ctg agc gtg gac tac ggc ctc aag ggg ctc gac        1298
Ser Leu Gly Pro Asp Leu Ser Val Asp Tyr Gly Leu Lys Gly Leu Asp
415                 420                 425                 430 atc gcc atg gcc gcc tac agc tcc gag ctt cag tac ctg gcg aat ccc        1346
Ile Ala Met Ala Ala Tyr Ser Ser Glu Leu Gln Tyr Leu Ala Asn Pro
            435                 440                 445 gtg acc aca cac gtg cac agc gcg gaa cag cac aac cag gac atc aac        1394
Val Thr Thr His Val His Ser Ala Glu Gln His Asn Gln Asp Ile Asn
        450                 455                 460
```

-continued

```
tct ctg gcg ctc atc tcc gcc cgc aag acg gag gag gcg ttg gat atc      1442
Ser Leu Ala Leu Ile Ser Ala Arg Lys Thr Glu Glu Ala Leu Asp Ile
            465                 470                 475 tta aag ctc atg atc gcc tcg cat tta aca gca atg tgc cag gcg gtg      1490
Leu Lys Leu Met Ile Ala Ser His Leu Thr Ala Met Cys Gln Ala Val
    480                 485                 490 gac ctt cgg cag ctc gaa gaa gcc cta gta aaa gtc gtg gag aat gtc      1538
Asp Leu Arg Gln Leu Glu Glu Ala Leu Val Lys Val Val Glu Asn Val
495                 500                 505                 510 gtt tcc acc ctt gca gac gaa tgc ggc ctc cct aac gac aca aag gcg      1586
Val Ser Thr Leu Ala Asp Glu Cys Gly Leu Pro Asn Asp Thr Lys Ala
                515                 520                 525 agg ctt tta tat gta gcc aaa gcg gtg cct gtt tac aca tac ctg gaa      1634
Arg Leu Leu Tyr Val Ala Lys Ala Val Pro Val Tyr Thr Tyr Leu Glu
            530                 535                 540 tcc ccc tgc gac ccc acg ctt ccc ctc ttg tta ggc ctg aaa cag tcc      1682
Ser Pro Cys Asp Pro Thr Leu Pro Leu Leu Leu Gly Leu Lys Gln Ser
        545                 550                 555 tgt ttc gat acc att ctg gct ctc cac aaa aaa gac ggc att gag acg      1730
Cys Phe Asp Thr Ile Leu Ala Leu His Lys Lys Asp Gly Ile Glu Thr
    560                 565                 570 gac acc ttg gtc gat cgg ctc gcc gag ttc gag aag cgg ctg tcc gac      1778
Asp Thr Leu Val Asp Arg Leu Ala Glu Phe Glu Lys Arg Leu Ser Asp
575                 580                 585                 590 cgc ctg gaa aac gag atg acg gca gtg agg gtt ttg tac gaa aag aaa      1826
Arg Leu Glu Asn Glu Met Thr Ala Val Arg Val Leu Tyr Glu Lys Lys
                595                 600                 605 ggg cat aaa acg gca gac aac aac gac gcc ctc gtg aga atc cag ggt      1874
Gly His Lys Thr Ala Asp Asn Asn Asp Ala Leu Val Arg Ile Gln Gly
            610                 615                 620 tcc aaa ttc ctt cct ttt tac aga ttt gtt cgg gaa gag ctc gac aca      1922
Ser Lys Phe Leu Pro Phe Tyr Arg Phe Val Arg Glu Glu Leu Asp Thr
        625                 630                 635 ggt gtg atg agt gcg aga aga gag cag acg ccg caa gag gac gtg cag      1970
Gly Val Met Ser Ala Arg Arg Glu Gln Thr Pro Gln Glu Asp Val Gln
    640                 645                 650 aaa gtg ttc gat gca att gcc gac ggc aga att acg gtg cct cta ctg      2018
Lys Val Phe Asp Ala Ile Ala Asp Gly Arg Ile Thr Val Pro Leu Leu
655                 660                 665                 670 cac tgc ctg caa ggg ttt ctc ggc caa cca aat ggg tgc gcc aac ggc      2066
His Cys Leu Gln Gly Phe Leu Gly Gln Pro Asn Gly Cys Ala Asn Gly
                675                 680                 685 gtc tagtcgttcc aaagtgtttg gaacaaatct gcgtgatttc tgcgtgaata           2119
Val tttgagtaga atttcagatt gttcggttcg tgtgatgttt gcagtagaaa ttccgcagaa    2179
gcgactgtag ctttgcgaga attgttagtt tgtgagtgaa atttatctga ttggcttcct    2239
atgtaaaccc taattaattt ttgttttaaa aggatccc                            2277

<210> SEQ ID NO 2
<211> LENGTH: 687
<212> TYPE: PRT
<213> ORGANISM: Taxus chinensis

<400> SEQUENCE: 2

Met Gly Phe Ala Val Glu Ser Arg Ser His Val Lys Asp Ile Leu Gly
1               5                   10                  15

Leu Ile Asn Ala Phe Asn Glu Val Lys Lys Ile Thr Val Asp Gly Thr
            20                  25                  30
```

```
Thr Pro Ile Thr Val Ala His Val Ala Leu Ala Arg Arg His Asp
        35                  40                  45
Val Lys Val Ala Leu Glu Ala Glu Gln Cys Arg Ala Arg Val Glu Thr
    50                  55                  60
Cys Ser Ser Trp Val Gln Arg Lys Ala Glu Asp Gly Ala Asp Ile Tyr
65                  70                  75                  80
Gly Val Thr Thr Gly Phe Gly Ala Cys Ser Ser Arg Arg Thr Asn Arg
                85                  90                  95
Leu Ser Glu Leu Gln Glu Ser Leu Ile Arg Cys Leu Leu Ala Gly Val
            100                 105                 110
Phe Thr Lys Gly Cys Ala Pro Ser Val Asp Glu Leu Pro Ala Thr Ala
        115                 120                 125
Thr Arg Ser Ala Met Leu Leu Arg Leu Asn Ser Phe Thr Tyr Gly Cys
    130                 135                 140
Ser Gly Ile Arg Trp Glu Val Met Glu Ala Leu Glu Lys Leu Leu Asn
145                 150                 155                 160
Ser Asn Val Ser Pro Lys Val Pro Leu Arg Gly Ser Val Ser Ala Ser
                165                 170                 175
Gly Asp Leu Ile Pro Leu Ala Tyr Ile Ala Gly Leu Leu Ile Gly Lys
            180                 185                 190
Pro Ser Val Ile Ala Arg Ile Gly Asp Asp Val Glu Val Pro Ala Pro
        195                 200                 205
Glu Ala Leu Ser Arg Val Gly Leu Arg Pro Phe Lys Leu Gln Ala Lys
    210                 215                 220
Glu Gly Leu Ala Leu Val Asn Gly Thr Ser Phe Ala Thr Ala Val Ala
225                 230                 235                 240
Ser Thr Val Met Tyr Asp Ala Asn Val Leu Leu Leu Val Glu Thr
                245                 250                 255
Leu Cys Gly Met Phe Cys Glu Val Ile Phe Gly Arg Glu Glu Phe Ala
            260                 265                 270
His Pro Leu Ile His Lys Val Lys Pro His Pro Gly Gln Ile Glu Ser
        275                 280                 285
Ala Glu Leu Leu Glu Trp Leu Leu Arg Ser Ser Pro Phe Gln Glu Leu
    290                 295                 300
Ser Arg Glu Tyr Tyr Ser Ile Asp Lys Leu Lys Lys Pro Lys Gln Asp
305                 310                 315                 320
Arg Tyr Ala Leu Arg Ser Ser Pro Gln Trp Leu Ala Pro Leu Val Gln
                325                 330                 335
Thr Ile Arg Asp Ala Thr Thr Thr Val Glu Thr Glu Val Asn Ser Ala
            340                 345                 350
Asn Asp Asn Pro Ile Ile Asp His Ala Asn Asp Arg Ala Leu His Gly
        355                 360                 365
Ala Asn Phe Gln Gly Ser Ala Val Gly Phe Tyr Met Asp Tyr Val Arg
    370                 375                 380
Ile Ala Val Ala Gly Leu Gly Lys Leu Leu Phe Ala Gln Phe Thr Glu
385                 390                 395                 400
Leu Met Ile Glu Tyr Tyr Ser Asn Gly Leu Pro Gly Asn Leu Ser Leu
                405                 410                 415
Gly Pro Asp Leu Ser Val Asp Tyr Gly Leu Lys Gly Leu Asp Ile Ala
            420                 425                 430
Met Ala Ala Tyr Ser Ser Glu Leu Gln Tyr Leu Ala Asn Pro Val Thr
        435                 440                 445
```

-continued

```
Thr His Val His Ser Ala Glu Gln His Asn Gln Asp Ile Asn Ser Leu
    450                 455                 460
Ala Leu Ile Ser Ala Arg Lys Thr Glu Glu Ala Leu Asp Ile Leu Lys
465                 470                 475                 480
Leu Met Ile Ala Ser His Leu Thr Ala Met Cys Gln Ala Val Asp Leu
                485                 490                 495
Arg Gln Leu Glu Glu Ala Leu Val Lys Val Val Glu Asn Val Val Ser
            500                 505                 510
Thr Leu Ala Asp Glu Cys Gly Leu Pro Asn Asp Thr Lys Ala Arg Leu
        515                 520                 525
Leu Tyr Val Ala Lys Ala Val Pro Val Tyr Thr Tyr Leu Glu Ser Pro
    530                 535                 540
Cys Asp Pro Thr Leu Pro Leu Leu Leu Gly Leu Lys Gln Ser Cys Phe
545                 550                 555                 560
Asp Thr Ile Leu Ala Leu His Lys Lys Asp Gly Ile Glu Thr Asp Thr
                565                 570                 575
Leu Val Asp Arg Leu Ala Glu Phe Glu Lys Arg Leu Ser Asp Arg Leu
            580                 585                 590
Glu Asn Glu Met Thr Ala Val Arg Val Leu Tyr Glu Lys Lys Gly His
        595                 600                 605
Lys Thr Ala Asp Asn Asn Asp Ala Leu Val Arg Ile Gln Gly Ser Lys
    610                 615                 620
Phe Leu Pro Phe Tyr Arg Phe Val Arg Glu Glu Leu Asp Thr Gly Val
625                 630                 635                 640
Met Ser Ala Arg Arg Glu Gln Thr Pro Gln Glu Asp Val Gln Lys Val
                645                 650                 655
Phe Asp Ala Ile Ala Asp Gly Arg Ile Thr Val Pro Leu Leu His Cys
            660                 665                 670
Leu Gln Gly Phe Leu Gly Gln Pro Asn Gly Cys Ala Asn Gly Val
        675                 680                 685
```

<210> SEQ ID NO 3
<211> LENGTH: 2411
<212> TYPE: DNA
<213> ORGANISM: Taxus chinensis

<400> SEQUENCE: 3

```
ttcagtttta tctcgctcaa gtttcaatct tttaatttta aagttatttt ccttgctctg      60
cgatggggtt tgccgtggaa tcgcgttctc acgtaaagga tatattgggg ctgatcaacg     120
cgttcaacga ggtgaagaaa attacagtag acggtacgac ccccatcacg gtggcccatg     180
tcgcggcgct ggcccggagg catgacgtga aggttgcgtt ggaggcggag caatgcagag     240
cccgtgtgga aacctgctct tcgtgggtgc agcgcaaggc ggaagacggc gccgacatat     300
acggcgtcac cacgggcttc ggcgcgtgct cgagccggag gaccaaccag ctgagcgagc     360
tgcaggagtc gctcatacgc tgcctgctcg cgggggtgtt tactaaagga tgcgcttcct     420
ccgtcgacga gctccccgcg accgccaccc gcagcgccat gctgctccgc cttaatagtt     480
ttaccctatg atgttccggc atccggtggg aggtcatgga agcgctggaa aagcttctca     540
acagcaatgt ctctcctaaa gtgcctctcc ggggttctgt gagcgcttcg ggagacctca     600
tcccgctcgc ctacattgca gggctcctga tcggaagcc tagcgtaatc gctcgcatag     660
gcgacgatgt cgaggtccct gcgcccgagg cgttgagcag ggtggggctt cggccattca     720
agctccaggc caaagaaggg ctggcgctcg tcaacggcac ctccttcgcc accgcggtcg     780
```

-continued

```
cctccaccgt catgtacgac gccaatgttc tgttgctgct cgtcgaaacg ctttgcggaa      840
tgttctgcga ggtgatcttt ggaagggagg agttcgcgca tccgctgatc cataaagtga      900
agccgcaccc gggccagatc gaatcggcgg agctgctcga gtggctgctg cggtcgagcc      960
cgtttcagga gctgtcgagg gagtattaca gtattgataa gctgaagaaa ccgaaacagg     1020
atcgctatgc tctgaggtcg agcccgcagt ggttggctcc tctggtgcag acaatcagag     1080
acgccaccac tacagtggag acggaggtca attccgccaa tgataacccc atcattgacc     1140
acgccaatga caggtaatgt atatcattcg tcgttaagca atctgccgac ttcatagaga     1200
ttccaaaact tctgacgaaa aagtggataa gacggggctc ctagaaagtt ttccttttaa     1260
agatgaacta tattttttta ttacggacta gatttcgacg gttttgtccg atccattggc     1320
agggctctcc atggtgcgaa tttccagggc agcgccgtcg gtttctacat ggactacgtg     1380
cgcatcgcag tcgccgggct ggggaaactc ttgttcgctc agttcacgga gctgatgatc     1440
gaatattaca gcaacggcct accggggaac ctctccctgg ggccggacct gagcgtggac     1500
tacggcctca aggggctcga catcgccatg gccgcctaca gctccgagct tcagtacctg     1560
gcgaatcccg tgaccacaca cgtgcacagc gcggaacagc acaaccagga catcaactct     1620
ctggcgctca tctccgcccg caagacggag gaggcgttgg atatcttaaa gctcatgatc     1680
gcctcgcatt taacagcaat gtgccaggcg gtggaccttc ggcagctcga agaagcccta     1740
gtaaaagtcg tggagaatgt cgtttccacc cttgcagacg aatgcggcct ccctaacgac     1800
acaaaggcga ggcttttata tgtagccaaa gcggtgcctg tttacacata cctggaatcc     1860
ccctgcgacc ccacgcttcc cctcttgtta ggcctgaaac agtcctgttt cgataccatt     1920
ctggctctcc acaaaaaaga cggcattgag acggacacct tggtcgatcg gctcgccgag     1980
ttcgagaagc ggctgtccga ccgcctggaa aacgagatga cggcagtgag ggttttgtac     2040
gaaaagaaag gcataaaaac ggcagacaac aacgacgccc tcgtaagaat ccagggttcc     2100
aaattccttc cttttttacag atttgttcgg gaagagctcg acacaggtgt gatgagtgcg     2160
agaagagagc agacgccgca agaggacgtg cagaaagtgt tcgatgcaat tgccgacggc     2220
agaattacgg tgcctctgct gcactgcctg caagggtttc tcggccaacc aaatgggtgc     2280
gccaacggcg tctagtcgtt ccaaagtgtt tggaacaaat ctgcgtgatt ctgcgtgaa      2340 tatttcagta gaatttcaga ttgttcggtt cgtgtgatgt ttgcagtaga aattccgcag     2400
aagcgactgt a                                                           2411
```

<210> SEQ ID NO 4
<211> LENGTH: 2233
<212> TYPE: DNA
<213> ORGANISM: Taxus media

<400> SEQUENCE: 4

```
atggggtttg ccgtggaatc gcgttctcac gtaaaggata tattggggct gatcaacacg       60
ttcaacgagg tgaagaaaat tacagtagac ggtacgaccc ccatcacggt ggcccatgtc      120
gcggcgctgg cccggaggca tgacgtgaag gttgcgttgg aggcggagca atgcagagcc      180
cgtgtggaaa cctgctcttc gtgggtgcaa cgcaaggcgg aagacggcgc cgacatatac      240
ggcgtcacca cgggcttcgg cgcgtgctcg agccggagga ccaaccagct gagcgagctg      300
caggagtcgc tcatacgctg cctgctcgcg ggggtgttta ctaaaggatg cgcttcctcc      360
gtcgacgagc tccccgcgac cgtcacccgc agcgccatgc tgctccgcct taatagtttt      420
acctatggat gttccggcat ccggtgggag gtcatggaag cgctggaaaa gcttctcaac      480
```

-continued

```
agcaatgtct ctcctaaagt gcctctccga ggatctgtga gcgcttcggg agacctcatc       540
ccgctcgcct acattgcagg gctcctgatc gggaaaccta gcgtaatcgc tcgcataggc       600
gacgatgtcg aggtccctgc gcccgaggcg ttgagcaggg tggggctgcg gccattcaag       660
ctccaggcca agaagggct ggcgctcgtc aacggcacct ccttcgccac cgcgctcgcc        720
tccaccgtca tgtacgacgc caatgttctg ttgctgctcg tcgaaacgct ttgcggaatg       780
ttctgcgagg tgatctttgg aagggaggag ttcgcgcatc cgctgatcca taaagtgaag       840
ccgcacccgg gccagatcga atcggcggag ctgctcgagt ggctgctgcg gtcgagcccg       900
tttcaggagc tgtcgaggga gtattacagt attgataagc tgaagaaacc gaaacaggat       960
cgctatgctc tgaggtcgag cccgcagtgg ttggctcctc tggtgcagac aatcagagac      1020
gccaccacta cagtggagac ggaggtcaat tccgccaatg ataaccccat cattgaccac      1080
gccaatgaca ggtaatgtac atcattcgtc gttaagcaat ctgccgactt catagagatt      1140
ccaaaacttc tgacaaaaaa gtggataaga tggggctcct agaaagtttt ccttttaaag      1200
atgaactata ttttttttata actgactaga tttcgctggt tttgtccgat ccattggcag     1260
ggctctccat ggtgcgaatt ccagggcag cgccgtcggc ttctacatgg actacgtgcg      1320
catcgcagtc gccgggctgg ggaaactctt gttcgctcag ttcacggagc tgatgatcga      1380
atattacagc aacggcctac cggggaacct ctccctgggg ccggacctga gcgtggacta      1440
cggcctcaag gggctcgaca tcgccatggc cgcctacagc tccgagcttc agtacctggc      1500
gaatcccgtg accacacacg tgcacagcgc ggaacagcac aaccaggaca tcaactctct      1560
ggcgctcatc tccgcccgca agacggatga ggcgttggat atcttaaagc tcatgatcgc      1620
ctcgcattta acagcaatgt gccaggcggt ggaccttcgg cagctcgaag aagccctagt      1680
aaaagtcgtg gagaatgtcg tttccaccct tgcagacgaa tgcggcctcc ctaacgacac      1740
aaaggcgagg cttttatatg tagccaaagc ggtgcctgtt tacacatacc tggaatcccc      1800
cagcgacccc acgcttcccc tcttgttagg cctgaaacaa tcctgtttcg attccattct      1860
ggctctccac aaaaaagacg gaattgagac ggacaccttg gtcgatcggc tcgccgagtt      1920
cgagaagcgg ctgtccgacc gcctggaaaa cgagatgacg gcagtgaggg ttttgtacga      1980
aaagaaaggg cataaaacgg cagacaacaa cgacgccctc gtgagaatcc agggttccaa      2040
attccttcct ttttacagat ttgttcggga cgagctcgac acaggtgtga tgagtgcgag      2100
aagagagcag acgccgcaag aggacgtgca gaaagtgttc gatgcaattg ccgacggcag      2160
aattacggtg cctctgctgc actgcctgca agggtttctc ggccaaccaa atgggtgcgc      2220
caacggcgtc tag                                                          2233
```

<210> SEQ ID NO 5
<211> LENGTH: 2235
<212> TYPE: DNA
<213> ORGANISM: Taxus canadensis

<400> SEQUENCE: 5

```
atggggtttg ccgtggaatc gcgttctcac gtaaaggata tattggggct gatcaacacg        60
ttcaacgagg tgaagaaaat tacagtagac ggtacgaccc ccatcacggt ggcccatgtc       120
gcggcgctgg cccggaggca tgacgtgaag gttgcgttgg aggcggagca atgcagagcc       180
cgtgtggaaa cctgctcttc gtgggtgcag cgcaaggcgg aagacggcgc cgacatatac       240
ggcgtcacca cgggctttgg cgcgtgctcg agccggagga ccaaccagct gagcgagctg       300
```

-continued

```
caggagtcgc ttatacgctg cctgctcgcg ggggtgttta ctaaaggatg cgcttcctcc    360
gtcgacgagc tccctgcgac cgtcacccgc agcgccatgc tgctccgcct taatagtttt    420
acctatggat gttccggcat ccggtgggag gtcatggaag cgctggaaaa gcttctcaac    480
agcaatgtct ctcctaaagt gcctctccga ggatctgtga gcgcttcggg agacctcatc    540
ccgctcgcct acattgcagg gctcctgatt gggaagccta gcgtaatcgc tcgcataggc    600
gacgatgtcg aggtccctgc gcccgaggcg ttgagcaggg tggggctgcg gccattcaag    660
ctccaggcca agaagggct ggcgctcgtc aacggcacct ccttcgccac cgcgctcgcc    720
tccaccgtca tgtacgacgc caatgttctg ttgctgctag tcgaaacgct ttgcggaatg    780
ttctgcgagg tgatctttgg aagggaggag ttcgcgcatc cgctgatcca taaagtgaag    840
ccgcacccag gccagatcga atcggcgag ctgctcgagt ggctgctgcg gtcgagcccg    900
tttcaggacc tgtcgaggga gtattacagt attgataagc tgaagaaacc gaaacaggat    960
cgctatgctc tgaggtcgag cccgcagtgg ttggctcctc tggtgcagac aatcagagac   1020
gccaccacta cagtggagac ggaggtcaat tccgccaatg ataacccat cattgaccac   1080
gccaatgaca ggtaatgcat atcattcgtc gttaagcaat ctgccgactt catagagatt   1140
ccaaaacttc tgacaaaaaa gtggataaga tggggctcct agaaagtttt cctttttaaag  1200
atgaactata tttttttata actgactaga tttcgctggt tttgtccgat ccattggcag   1260
ggctctccat ggtgcgaatt ccagggcag cgccgtcggc ttctacatgg actacgtgcg    1320
catcgcagtc gccgggctgg ggaaactctt gttcgctcag ttcacggagc tgatgatcga   1380
atattacagc aacggcctac cggggaacct ctccctgggg ccggacctga gcgtggacta   1440
cggcctcaag gggctcgaca tcgccatggc cgcctacagc tccgagcttc agtacctggc   1500
gaatcccgtg accacacacg tgcacagcgc ggaacagcac aaccaggaca tcaactctct   1560
ggcgctcatc tccgcccgca agacggatga ggcgttggat atcttaaagc tcatgatcgc   1620
ctcgcattta acagcaatgt gccaggcggt ggaccttcgg cagctcgaag aagccctagt   1680
aaaagtcgtg gagaatgtcg tttccaccct tgcagacgaa tgcggcctcc ctaacgacac   1740
aaaggcgagg cttttatatg tagccaaagc ggtgcctgtt tacacatacc tggaatcccc   1800
ctgcgacct acgcttcccc tcttgttagg cctgaaacag tcctgtttcg attccattct    1860
ggctctccac aaaaaagacg gcattgagac ggacaccttg gtggatcggc tcgccgagtt   1920
cgagaagcgg ctgtccgacc gcctggaaaa cgagatgacg gcagtgaggg ttttgtacga   1980
aaagaaaggg cataaaactg cagacaacaa cgacgccctc gtgagaatcc agggttccaa   2040
attccttcct ttttacagat tgttcggga cgagctcgac acaggtgtga tgagtgcgag   2100
aagagagcag acgccgcaag aggacgtgca gaaagtgttc gatgcaattg ccgacggcag   2160
aattacggtg cctctgctgc actgcctgca agggtttctc ggccaaccaa atgggtgcgc   2220
caacggcgtc tagac                                                    2235
```

<210> SEQ ID NO 6
<211> LENGTH: 10
<212> TYPE: PRT
<213> ORGANISM: Taxus chinensis

<400> SEQUENCE: 6

Leu Leu Asn Ser Asn Val Ser Pro Met Met
1               5                   10

<210> SEQ ID NO 7

```
<211> LENGTH: 7
<212> TYPE: PRT
<213> ORGANISM: Taxus chinensis

<400> SEQUENCE: 7

Glu Tyr Tyr Ser Ile Asp Lys
1               5

<210> SEQ ID NO 8
<211> LENGTH: 6
<212> TYPE: PRT
<213> ORGANISM: Taxus chinensis

<400> SEQUENCE: 8

Leu Ala Glu Phe Glu Lys
1               5

<210> SEQ ID NO 9
<211> LENGTH: 13
<212> TYPE: PRT
<213> ORGANISM: Taxus chinensis

<400> SEQUENCE: 9

Leu Ser Asp Arg Leu Glu Asn Glu Met Thr Ala Val Arg
1               5                   10

<210> SEQ ID NO 10
<211> LENGTH: 15
<212> TYPE: PRT
<213> ORGANISM: Taxus chinensis

<400> SEQUENCE: 10

Thr Cys Ala Ser Ser Val Asp Glu Leu Pro Ala Thr Ala Thr Arg
1               5                   10                  15

<210> SEQ ID NO 11
<211> LENGTH: 4
<212> TYPE: PRT
<213> ORGANISM: Taxus chinensis

<400> SEQUENCE: 11

Gly Ala Thr Arg
1

<210> SEQ ID NO 12
<211> LENGTH: 4
<212> TYPE: PRT
<213> ORGANISM: Taxus chinensis

<400> SEQUENCE: 12

Val Gly Leu Arg
1

<210> SEQ ID NO 13
<211> LENGTH: 12
<212> TYPE: PRT
<213> ORGANISM: Taxus chinensis
<220> FEATURE:
<221> NAME/KEY: misc_feature
<222> LOCATION: (9)..(9)
<223> OTHER INFORMATION: Xaa can be any naturally occurring amino acid

<400> SEQUENCE: 13

Leu Asn Ser Phe Thr Tyr Gly Cys Xaa Gly Ile Arg
1               5                   10
```

<210> SEQ ID NO 14
<211> LENGTH: 10
<212> TYPE: PRT
<213> ORGANISM: Taxus chinensis

<400> SEQUENCE: 14

Phe Phe Ala Val Glu Ala Arg Ser His Val
1               5                   10

<210> SEQ ID NO 15
<211> LENGTH: 6
<212> TYPE: PRT
<213> ORGANISM: Taxus chinensis

<400> SEQUENCE: 15

Leu Glu Asn Glu Met Thr
1               5

<210> SEQ ID NO 16
<211> LENGTH: 17
<212> TYPE: DNA
<213> ORGANISM: Artificial Sequence
<220> FEATURE:
<223> OTHER INFORMATION: Synthesized Degenerate Oligonucleotide.
<220> FEATURE:
<221> NAME/KEY: misc_feature
<222> LOCATION: (3)..(3)
<223> OTHER INFORMATION: n is a, c, g, or t

<400> SEQUENCE: 16
ytngaraayg aratgac                                                    17

<210> SEQ ID NO 17
<211> LENGTH: 8
<212> TYPE: PRT
<213> ORGANISM: Taxus chinensis

<400> SEQUENCE: 17

Leu Glu Asn Glu Met Thr Ala Val
1               5

<210> SEQ ID NO 18
<211> LENGTH: 21
<212> TYPE: DNA
<213> ORGANISM: Artificial Sequence
<220> FEATURE:
<223> OTHER INFORMATION: Synthesized Degenerate Oligonucleotide.
<220> FEATURE:
<221> NAME/KEY: misc_feature
<222> LOCATION: (3)..(3)
<223> OTHER INFORMATION: n is a, c, g, or t

<400> SEQUENCE: 18
ytngaraayg aratgacgcg t                                               21

<210> SEQ ID NO 19
<211> LENGTH: 7
<212> TYPE: PRT
<213> ORGANISM: Taxus chinensis

<400> SEQUENCE: 19

Leu Asn Ser Phe Thr Tyr Gly
1               5

<210> SEQ ID NO 20
<211> LENGTH: 17

```
<212> TYPE: DNA
<213> ORGANISM: Artificial Sequence
<220> FEATURE:
<223> OTHER INFORMATION: Synthesized Degenerate Oligonucleotide.
<220> FEATURE:
<221> NAME/KEY: misc_feature
<222> LOCATION: (12)..(12)
<223> OTHER INFORMATION: n is a, c, g, or t

<400> SEQUENCE: 20
ytaaywbttc antaygg                                                        17

<210> SEQ ID NO 21
<211> LENGTH: 7
<212> TYPE: PRT
<213> ORGANISM: Taxus chinensis

<400> SEQUENCE: 21

Leu Asn Ser Phe Thr Tyr Gly
1               5

<210> SEQ ID NO 22
<211> LENGTH: 18
<212> TYPE: DNA
<213> ORGANISM: Artificial Sequence
<220> FEATURE:
<223> OTHER INFORMATION: Synthesized Degenerate Oligonucleotide.
<220> FEATURE:
<221> NAME/KEY: misc_feature
<222> LOCATION: (13)..(13)
<223> OTHER INFORMATION: n is a, c, g, or t

<400> SEQUENCE: 22
ytaaywbtty cantaygg                                                       18

<210> SEQ ID NO 23
<211> LENGTH: 6
<212> TYPE: PRT
<213> ORGANISM: Taxus chinensis

<400> SEQUENCE: 23

Leu Leu Asn Ser Asn Val
1               5

<210> SEQ ID NO 24
<211> LENGTH: 15
<212> TYPE: DNA
<213> ORGANISM: Artificial Sequence
<220> FEATURE:
<223> OTHER INFORMATION: Synthesized Degenerate Oligonucleotide.
<220> FEATURE:
<221> NAME/KEY: misc_feature
<222> LOCATION: (10)..(10)
<223> OTHER INFORMATION: n is a, c, g, or t

<400> SEQUENCE: 24
ytytaaywbn aaygt                                                          15

<210> SEQ ID NO 25
<211> LENGTH: 7
<212> TYPE: PRT
<213> ORGANISM: Taxus chinensis

<400> SEQUENCE: 25

Leu Leu Asn Ser Asn Val Ser
1               5
```

```
<210> SEQ ID NO 26
<211> LENGTH: 17
<212> TYPE: DNA
<213> ORGANISM: Artificial Sequence
<220> FEATURE:
<223> OTHER INFORMATION: Synthesized Degenerate Oligonucleotide.
<220> FEATURE:
<221> NAME/KEY: misc_feature
<222> LOCATION: (15)..(15)
<223> OTHER INFORMATION: n is a, c, g, or t

<400> SEQUENCE: 26
ytytaaywba aygtncc                                                17

<210> SEQ ID NO 27
<211> LENGTH: 6
<212> TYPE: PRT
<213> ORGANISM: Taxus chinensis

<400> SEQUENCE: 27

Glu Tyr Tyr Ser Ile Asp
1               5

<210> SEQ ID NO 28
<211> LENGTH: 17
<212> TYPE: DNA
<213> ORGANISM: Artificial Sequence
<220> FEATURE:
<223> OTHER INFORMATION: Synthesized Degenerate Oligonucleotide.
<220> FEATURE:
<221> NAME/KEY: misc_feature
<222> LOCATION: (12)..(12)
<223> OTHER INFORMATION: n is a, c, g, or t

<400> SEQUENCE: 28
gamtaytayw bnayhga                                                17

<210> SEQ ID NO 29
<211> LENGTH: 20
<212> TYPE: DNA
<213> ORGANISM: Artificial Sequence
<220> FEATURE:
<223> OTHER INFORMATION: Synthesized Degenerate Oligonucleotide.
<220> FEATURE:
<221> NAME/KEY: misc_feature
<222> LOCATION: (12)..(12)
<223> OTHER INFORMATION: n is a, c, g, or t

<400> SEQUENCE: 29
gamtaytayw bnathgayaa                                             20

<210> SEQ ID NO 30
<211> LENGTH: 17
<212> TYPE: DNA
<213> ORGANISM: Bacteriophage M13

<400> SEQUENCE: 30
tgaccggcag caaaatg                                                17

<210> SEQ ID NO 31
<211> LENGTH: 28
<212> TYPE: DNA
<213> ORGANISM: Taxus chinensis

<400> SEQUENCE: 31
tgcatcgaac actttctgca cgtcctct                                    28
```

```
<210> SEQ ID NO 32
<211> LENGTH: 27
<212> TYPE: DNA
<213> ORGANISM: Taxus chinensis

<400> SEQUENCE: 32
tccttgctct catattatgg ggtttgc                                           27

<210> SEQ ID NO 33
<211> LENGTH: 33
<212> TYPE: DNA
<213> ORGANISM: Taxus chinensis

<400> SEQUENCE: 33
gggatccttt taaaacaaaa attaattagg gtt                                    33

<210> SEQ ID NO 34
<211> LENGTH: 21
<212> TYPE: DNA
<213> ORGANISM: Taxus chinensis

<400> SEQUENCE: 34
tcagttttat ctcgctcaag t                                                 21

<210> SEQ ID NO 35
<211> LENGTH: 20
<212> TYPE: DNA
<213> ORGANISM: Taxus chinensis

<400> SEQUENCE: 35
tacagtcgct tctgcggaat                                                   20

<210> SEQ ID NO 36
<211> LENGTH: 21
<212> TYPE: DNA
<213> ORGANISM: Taxus chinensis

<400> SEQUENCE: 36
atggggtttg ccgtggaatc g                                                 21

<210> SEQ ID NO 37
<211> LENGTH: 18
<212> TYPE: DNA
<213> ORGANISM: Taxus chinensis

<400> SEQUENCE: 37
ctagacgccg ttggcgca                                                     18
```